(12) United States Patent
Resconi et al.

(10) Patent No.: US 7,834,205 B2
(45) Date of Patent: Nov. 16, 2010

(54) METALLOCENE COMPOUNDS

(75) Inventors: Luigi Resconi, Ferrara (IT); Francesca Focante, Filottrano Ancona (IT); Davide Balboni, Ferrara (IT); Ilya E. Nifant'ev, Moscow (RU); Pavel V. Ivchenko, Moscow (RU); Vladimir Bagrov, Moscow (RU)

(73) Assignee: Basell Polyolifine GmbH, Wesseling (DE)

( * ) Notice: Subject to any disclaimer, the term of this patent is extended or adjusted under 35 U.S.C. 154(b) by 9 days.

(21) Appl. No.: 12/226,095

(22) PCT Filed: Apr. 6, 2007

(86) PCT No.: PCT/EP2007/053422
§ 371 (c)(1),
(2), (4) Date: Oct. 7, 2008

(87) PCT Pub. No.: WO2007/116034
PCT Pub. Date: Oct. 18, 2007

(65) Prior Publication Data
US 2009/0275712 A1  Nov. 5, 2009

Related U.S. Application Data

(60) Provisional application No. 60/795,865, filed on Apr. 28, 2006.

(30) Foreign Application Priority Data

Apr. 12, 2006  (EP) .................... 06112576

(51) Int. Cl.
C07F 17/00 (2006.01)
C08F 4/6592 (2006.01)

(52) U.S. Cl. .................... 556/53; 526/160; 526/172; 526/943; 502/152

(58) Field of Classification Search ............ 556/53; 526/160, 165, 172, 943; 502/152
See application file for complete search history.

(56) References Cited

U.S. PATENT DOCUMENTS

| | | | |
|---|---|---|---|
| 5,698,487 A | 12/1997 | Sacchetti et al. | |
| 5,770,753 A | 6/1998 | Küber et al. | |
| 5,786,432 A | 7/1998 | Küber et al. | |
| 5,840,644 A | 11/1998 | Küber et al. | |
| 5,840,948 A | 11/1998 | Rohrmann et al. | |
| 6,051,727 A | 4/2000 | Küber et al. | |
| 6,057,408 A | 5/2000 | Winter et al. | |
| 6,242,544 B1 | 6/2001 | Küber et al. | |
| 6,255,506 B1 | 7/2001 | Küber et al. | |
| 6,399,533 B2 | 6/2002 | Sacchetti et al. | |
| 6,423,660 B1 | 7/2002 | Albizzati et al. | |
| 6,444,604 B1 | 9/2002 | Albizzati et al. | |
| 6,492,539 B1 | 12/2002 | Bingel et al. | |
| 6,559,252 B1 | 5/2003 | Horton et al. | |
| 6,608,224 B2 | 8/2003 | Resconi et al. | |
| 6,774,194 B2 | 8/2004 | Albizzati et al. | |
| 6,787,618 B1 | 9/2004 | Winter et al. | |
| 6,841,501 B2 | 1/2005 | Resconi et al. | |
| 6,878,786 B2 | 4/2005 | Resconi et al. | |
| 6,953,829 B2 | 10/2005 | Kratzer et al. | |
| 6,963,017 B2 | 11/2005 | Bingel et al. | |
| 7,038,070 B2 | 5/2006 | Bingel et al. | |
| 7,053,160 B1 | 5/2006 | Bingel et al. | |
| 7,101,940 B2 | 9/2006 | Schottek et al. | |
| 7,141,527 B1 | 11/2006 | Van Baar et al. | |
| 7,157,591 B2 * | 1/2007 | Burkhardt et al. ............. 556/53 |
| 7,452,949 B2 | 11/2008 | Okumura et al. | |
| 2006/0052553 A1 | 3/2006 | Resconi et al. | |
| 2006/0252637 A1 | 11/2006 | Okumura | |
| 2009/0171047 A1 | 7/2009 | Resconi et al. | |

FOREIGN PATENT DOCUMENTS

| | | |
|---|---|---|
| DE | 19962814 | 6/2001 |
| DE | 19962910 | 7/2001 |
| EP | 576970 | 1/1994 |
| EP | 633272 | 1/1995 |
| EP | 776913 | 6/1997 |
| WO | 91/02012 | 2/1991 |
| WO | 92/00333 | 1/1992 |

(Continued)

OTHER PUBLICATIONS

L. Resconi et al., "Selectivity in Propene Polymerization with Metallocene Catalysts;" *Chem. Rev.*, vol. 100(4), p. 1253-1345 (2000).

(Continued)

*Primary Examiner*—Caixia Lu
(74) *Attorney, Agent, or Firm*—William R. Reid

(57) ABSTRACT

A bridged metallocene compound of formula (I)

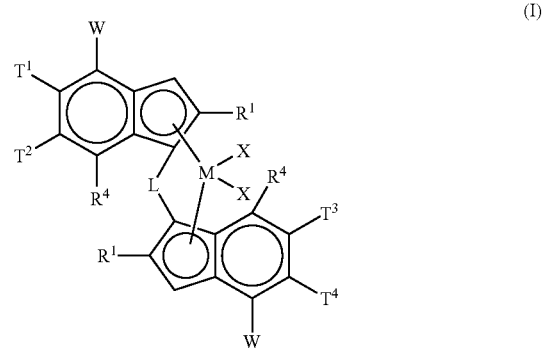

wherein:
M is a transition metal; X, is a hydrogen atom, a halogen atom, or a hydrocarbon group optionally containing heteroatoms; L is a divalent bridging group; $R^1$ is a linear $C_1$-$C_{40}$ hydrocarbon radical optionally containing heteroatoms; $T^1$ and $T^4$ are a oxygen, sulfur atom or a $C(R^{18})_3$ group; wherein $R^{18}$, are hydrogen atoms or a $C_1$-$C_{40}$ hydrocarbon radical; $T^3$ and $T^4$ are $C_1$-$C_{40}$ hydrocarbon radicals; $R^4$ is a hydrogen atom or a $C_1$-$C_{40}$ hydrocarbon radical; W is an aromatic 5 or 6 membered ring.

8 Claims, No Drawings

FOREIGN PATENT DOCUMENTS

| | | |
|---|---|---|
| WO | 95/32995 | 12/1995 |
| WO | 98/40331 | 9/1998 |
| WO | 99/21899 | 5/1999 |
| WO | 00/31090 | 6/2000 |
| WO | 01/21674 | 3/2001 |
| WO | 01/62764 | 8/2001 |
| WO | 03/050131 | 6/2003 |
| WO | WO 03/050131 * | 6/2003 |
| WO | 2004/050724 | 6/2004 |
| WO | 2004/106351 | 12/2004 |
| WO | 2005/058916 | 6/2005 |
| WO | 2006/097500 | 9/2006 |
| WO | 2007/107448 | 9/2007 |

OTHER PUBLICATIONS

C. Carman et al., "Monomer Sequence Distribution in Ethylene-Propylene Rubber Measured by $^{13}$C NMR. 3. Use of Reaction Probability Model," *Macromolecules*, vol. 10(3), p. 536-544 (1977).

Kakugo et al., "$^{13}$C NMR Determination of Monomer Sequence Distribution in Ethylene-Propylene Copolymers Prepared with δ-TiCl$_3$-Al(C$_2$H$_5$)$_2$Cl," *Macromolecules*, vol. 15(4), p. 1150-1152 (1982).

I. Triotto et al., "$^{13}$C NMR Studies of Ethylene-Propylene Copolymers Prepared with Homogeneous Metallocene-Based Ziegler-Natta Catalysts," *Macromolecules*, vol. 28(9), p. 3342-3350 (1995).

F. Forlini et al., "$^{13}$C NMR studies of zirconocene-catalyzed propylene/1-hexene copolymers: in-depth investigation of the effect of solvent polarity." *Macromol. Chem. Phys.*, vol. 201(4), p. 401-408 (2000).

V. Izmer et al., "Palladium-Catalyzed Pathways to Aryl-Substituted Indenes: Efficient Synthesis of Ligands and the Respective *ansa*-Zirconocenes," *Organometallics*, vol. 25(5), p. 1217-1229 (2006).

J. Randall, "A Review of High Resolution Liquid $^{13}$Carbon Nuclear Magnetic Resonance Characterizations of Ethylene-Based Polymers," *JMS-Rev. Macromol. Chem. Phys.*, vol. C29(2&3), p. 201-317 (1989).

J. Randall, "A $^{13}$C NMR Determination of the Comonomer Sequence Distributions in Propylene-Butene-1 Copolymers," *Macromolecules*, vol. 11(3), p. 592-597 (1978).

* cited by examiner

METALLOCENE COMPOUNDS

This application is the U.S. national phase of International Application PCT/EP2007/053422, filed Apr. 6, 2007, claiming priority to European Application 06112576.1 filed Apr. 12, 2006 and the benefit under 35 U.S.C. 119(e) of U.S. Provisional Application No. 60/795,865, filed Apr. 28, 2006; the disclosures of International Application PCT/EP2007/053422, European Application 06112576.1 and U.S. Provisional Application No. 60/795,865, each as filed, are incorporated herein by reference.

The present invention relates to a class of chiral bridged bis indenyl metallocene compounds, wherein the indenyl moieties are, in particular, substituted in positions 2 by a linear alkyl group and 4 by an aromatic moiety and they are further substituted in positions 5 and 6. The present invention further relates to the catalyst system thereof and the polymerization process therefrom.

Metallocene compounds are well known in the art as catalyst components for the polymerization of olefins. WO 03/050131 relates to a class of bis indenyl metallocene compounds wherein the indenyl moieties are at least substituted in position 4 and 5. However WO 03/050131 reports that position 6 can be only optionally substituted and moreover it does not report that the substituents on position 6 can be a secondary or a tertiary carbon atoms. PCT/EP03/12236 relates to a bis indenyl metallocene compound substituted at least in positions 2, 5 and 6, wherein the substituents in positions 5 and 6 form a condensed ring. However the substituent in position 4 is defined only in a generic way and in the compounds exemplified in the examples it is always a hydrogen atom. In PCT/EP2004/013827 a class of bis indenyl metallocene compounds wherein the indenyl moieties are substituted in position 5 and 6 by a condensed ring is disclosed. PCT/EP2004/013827 is mainly focused on structures wherein the position 1 of the two indenyl moieties are different, in particular one is branched in alpha position.

The compounds disclosed in these documents are able to polymerize alpha-olefins, in particular propylene. However there is still the need to find a new class of metallocene compounds able to polymerize olefins in higher yields and to produce polymers having very high molecular weight.

An object of the present invention is a bridged metallocene compound of formula (I)

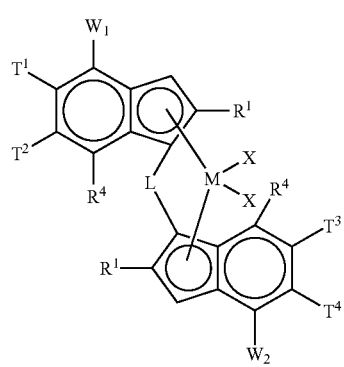

(I)

wherein:

M is an atom of a transition metal selected from those belonging to group 3, 4, or to the lanthanide or actinide groups in the Periodic Table of the Elements; preferably M is zirconium, titanium or hafnium;

X, equal to or different from each other, is a hydrogen atom, a halogen atom, a R, OR, $OSO_2CF_3$, OCOR, SR, $NR_2$ or $PR_2$ group wherein R is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical; optionally containing heteroatoms belonging to groups 13-17 of the Periodic Table of the Elements; or two X groups can be joined together to form a group OR'O wherein R' is a $C_1$-$C_{20}$-alkylidene, $C_6$-$C_{20}$-arylidene, $C_7$-$C_{20}$-alkylarylidene, or $C_7$-$C_{20}$-arylalkylidene radical; preferably X is a hydrogen atom, a halogen atom or R group; more preferably X is chlorine or a methyl radical;

L is a divalent bridging group selected from $C_1$-$C_{20}$ alkylidene, $C_3$-$C_{20}$ cycloalkylidene, $C_6$-$C_{20}$ arylidene, $C_7$-$C_{20}$ alkylarylidene, or a $C_7$-$C_{20}$ arylalkylidene radicals, optionally containing heteroatoms belonging to groups 13-17 of the Periodic Table of the Elements, or it is a silylidene radical containing up to 5 silicon atoms; preferably L is $Si(R^{11})_2$ wherein $R^{11}$ is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical; more preferably L is $Si(CH_3)_2$ or $SiPh_2$;

$R^1$ is a linear $C_1$-$C_{40}$ hydrocarbon radical optionally containing heteroatoms belonging to groups 13-17 of the Periodic Table of the Elements such as methyl or ethyl radical or an alpha branched aryl or arylalkyl radical containing from 2 to 20 carbon atoms optionally containing O, N, S, P and Se atoms, in particular O, N and S atoms such as 2(5-Me-thiophenyl) or 2(5-Me-furanyl) radicals; preferably $R^1$ is a linear $C_1$-$C_{20}$-alkyl, $C_2$-$C_{40}$ alkenyl, $C_2$-$C_{40}$ alkynyl radical, preferably $R^1$ is a linear $C_1$-$C_{10}$-alkyl radical; more preferably $R^1$ is a methyl, or ethyl radical;

$T^1$ and $T^4$, equal to or different from each other, are an $OR^2$, a $SR^2$ or a $C(R^{18})_3$ group; preferably $T^1$ and $T^4$ are an $OR^2$ or an $SR^2$ group;

wherein $R^2$, equal to or different from each other, is a $C_1$-$C_{40}$ hydrocarbon radicals; preferably $R^2$ is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals; more preferably $R^2$ is a linear or branched $C_1$-$C_{20}$-alkyl radical, such as methyl, ethyl, isopropyl, trimethylsilyl, or tertbutyl radical;

$R^{18}$, equal to or different from each other, are hydrogen atoms or a $C_1$-$C_{40}$ hydrocarbon radical optionally containing one or more heteroatoms belonging to groups 13-17 of the Periodic Table of the Elements; preferably $R^{18}$ is a hydrogen atom or a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical, optionally containing one or more heteroatoms belonging to groups 13-17 of the Periodic Table of the Elements; more preferably $R^{18}$ is a hydrogen atom or a linear or branched, $C_1$-$C_{20}$-alkyl radical; more preferably $R^{18}$ is a hydrogen atom or a methyl or ethyl radical;

$T^2$ and $T^3$, equal to or different from each other, are $C_1$-$C_{40}$ hydrocarbon radical optionally containing one or more heteroatoms belonging to groups 13-17 of the Periodic Table of the Elements; preferably $T^2$ and $T^3$ are linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals, optionally containing one or more heteroatoms belonging to groups 13-17 of the Periodic Table of the Elements; more preferably $T^2$ and $T^3$ are linear or branched, $C_1$-$C_{20}$-alkyl radicals;

$R^4$ is a hydrogen atom or a $C_1$-$C_{40}$ hydrocarbon radical optionally containing heteroatoms belonging to groups 13-17 of the Periodic Table of the Elements; preferably $R^4$ is a hydrogen atom or a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical optionally containing heteroatoms belonging to groups 13-17 of the Periodic Table of the Elements; preferably $R^4$ is a hydrogen atom a $C_1$-$C_{10}$-alkyl or a $C_6$-$C_{40}$-aryl radical; more preferably $R^4$ is an hydrogen atom;

$W^1$ and $W^2$, equal or different from each other, are aromatic 5 or 6 membered rings that can contain heteroatoms belonging to groups 15-16 of the Periodic Table of the Elements; the valence of each atom of said ring is substituted with hydrogen atom or it can optionally be substituted with $R^5$ groups, wherein $R^5$, equal to or different from each other, are $C_1$-$C_{40}$ hydrocarbon radicals optionally containing heteroatoms belonging to groups 13-17 of the Periodic Table of the Elements; preferably $R^5$, are linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals optionally containing heteroatoms belonging to groups 13-17 of the Periodic Table of the Elements;

Preferably $W^1$ and $W^2$ are selected from the group comprising the following moieties of formula (Wa), (Wb) and (Wc):

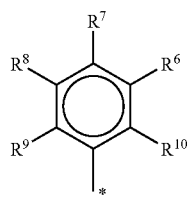
(Wa)

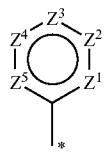
(Wb)

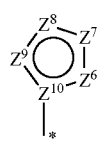
(Wc)

wherein the * represents the point in which the moiety is bonded to the indenyl moiety of the compound of formula (I);

$R^6$, $R^7$, $R^8$, $R^9$ and $R^{10}$, equal to or different from each other, are hydrogen atoms or $C_1$-$C_{40}$ hydrocarbon radicals optionally containing heteroatoms belonging to groups 13-17 of the Periodic Table of the Elements; preferably $R^6$, $R^7$, $R^8$, $R^9$ and $R^{10}$, are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals optionally containing heteroatoms belonging to groups 13-17 of the Periodic Table of the Elements;

$Z^1$ is a nitrogen atom or a $CR^{10}$ group; $Z^2$ is a nitrogen atom or a $CR^6$ group; $Z^3$ is a nitrogen atom or a $CR^7$ group; $Z^4$ is a nitrogen atom or a $CR^8$ group; $Z^5$ is a nitrogen atom or a $CR^9$ group; provided that no more than 2 groups among $Z^1$, $Z^2$, $Z^3$, $Z^4$ and $Z^5$ are nitrogen atoms, preferably no more than one group among $Z^1$, $Z^2$, $Z^3$, $Z^4$ and $Z^5$ is a nitrogen atom;

$Z^6$ is an oxygen atom, a sulfur atom, a $NR^{13}$ group or a $CR^{13}$ group; $Z^7$ is an oxygen atom, a sulfur atom, a $NR^{14}$ group or a $CR^{14}$ group; $Z^8$ is an oxygen atom, a sulfur atom, a $NR^{15}$ group or a $CR^{15}$ group; $Z^9$ is an oxygen atom, a sulfur atom, a $NR^{16}$ group or a $CR^{16}$ group;

$Z^{10}$ is a nitrogen atom or a carbon atom that bonds the indenyl moiety of the structure of formula (I); with the proviso that not more than 1 group among $Z^6$, $Z^7$, $Z^8$, $Z^9$ or $Z^{10}$ is a sulfur atom, an oxygen atom or a nitrogen-containing group atom selected from $NR^{13}$, $NR^{14}$, $NR^{15}$, $NR^{16}$, and a nitrogen atom; $R^{13}$, $R^{14}$, $R^{15}$ and $R^{16}$, equal to or different from each other, are hydrogen atoms or $C_1$-$C_{40}$ hydrocarbon radicals optionally containing heteroatoms belonging to groups 13-17 of the Periodic Table of the Elements; preferably $R^{13}$, $R^{14}$, $R^{15}$ and $R^{16}$, are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals optionally containing heteroatoms belonging to groups 13-17 of the Periodic Table of the Elements; more preferably $R^{13}$, $R^{14}$, $R^{15}$ and $R^{16}$ are hydrogen atoms, $C_1$-$C_{40}$-alkyl or $C_6$-$C_{40}$-aryl radicals;

In the moiety of formula (Wa), in a preferred embodiment, $R^7$ is a $C_1$-$C_{40}$-alkyl radical, preferably a branched $C_1$-$C_{40}$-alkyl radical, more preferably $R^7$ is a branched $C_1$-$C_{40}$-alkyl radical wherein the carbon atom in position alpha is a tertiary carbon atom such as a tertbutyl radical, and $R^6$, $R^8$, $R^9$ and $R^{10}$ are hydrogen atoms;

In a further preferred embodiment $R^{10}$ and $R^8$ are $C_1$-$C_{40}$-alkyl radicals, preferably they are linear $C_1$-$C_{40}$ alkyl radicals such as methyl radicals and $R^7$, $R^8$ and $R^9$ are hydrogen radicals:

In a further preferred embodiment $R^6$, $R^7$ and $R^8$ are linear or branched $C_1$-$C_{40}$-alkyl radicals such as methyl or tertbutyl radicals and $R^{10}$ and $R^9$ are hydrogen atoms.

In a further preferred embodiment $R^6$, $R^7$, $R^8$, $R^9$ and $R^{10}$ are hydrogen atoms;

In the moiety of formula (Wb), in a preferred embodiment, $Z^1$ is a nitrogen atom and $Z^2$, $Z^3$, $Z^4$ and $Z^5$ are respectively $CR^6$, $CR^7$, $CR^8$ and $CR^9$ wherein the meaning of $R^6$, $R^7$, $R^8$, and $R^9$ is described above; in a further preferred embodiment $Z^3$ is a nitrogen atom and $Z^1$, $Z^2$, $Z^4$ and $Z^5$ are respectively $CR^{10}$, $CR^6$, $CR^8$ and $CR^9$ wherein the meaning of $R^{10}$, $R^6$, $R^8$, and $R^9$ is described above; in a further preferred embodiment $Z^2$ is a nitrogen atom and $Z^1$, $Z^3$, $Z^4$ and $Z^5$ are respectively $CR^{10}$, $CR^7$, $CR^8$ and $CR^9$ wherein the meaning of $R^{10}$, $R^7$, $R^8$, and $R^9$ is described above;

In the moiety of formula (Wc) in a preferred embodiment $Z^6$ is an oxygen atom, a sulfur atom, a $NR^{16}$ group; preferably it is a sulfur atom or a $NR^{16}$; wherein $R^{16}$ is preferably a $C_1$-$C_{40}$-alkyl radical; more preferably $Z^6$ is a sulfur atom; and $Z^7$, $Z^8$, $Z^9$ and $Z^{10}$ are respectively a $CR^{14}$, $CR^{15}$, $CR^{16}$ and a carbon atom, wherein $R^{14}$ is a hydrogen atom or a $C_1$-$C_{40}$-alkyl radical such as methyl or ethyl; and $R^{15}$ and $R^{16}$ are hydrogen atoms or $C_1$-$C_{40}$-alkyl radicals.

In a preferred embodiment of the present invention in the compounds of formula (I) $T^1$ and $T^4$, equal to or different from each other, are an $OR^2$, or a $SR^2$ wherein $R^2$ is described above and $T^2$ and $T^3$, equal to or different from each other, are linear $C_1$-$C_{20}$-alkyl alkyl radicals, such as methyl or ethyl radicals.

In a further preferred embodiment $T^1$ and $T^4$, equal to or different from each other, are an $OR^2$, a $SR^2$ or a $C(R^{18})_3$ group; preferably $T^1$ and $T^4$ are an $OR^2$ or an $SR^1$ groups; and $T^2$ and $T^3$ equal to or different from each other are a $C(R^{19})_2 R^{18}$ group wherein $R^{18}$ has been described above and $R^{19}$ is a $C_1$-$C_{20}$ hydrocarbon radical optionally containing one or more heteroatoms belonging to groups 13-17 of the Periodic Table of the Elements; preferably $R^{19}$ is a linear or branched, cyclic or acyclic, $C_1$-$C_{20}$-alkyl, $C_2$-$C_{20}$ alkenyl, $C_2$-$C_{20}$ alkynyl, $C_6$-$C_{20}$-aryl, $C_7$-$C_{20}$-alkylaryl or $C_7$-$C_{20}$-arylalkyl radical, optionally containing one or more heteroatoms belonging to groups 13-17 of the Periodic Table of the Elements; or two $R^{19}$ radical can join together to form a $C_4$-$C_6$ membered ring wherein optionally one carbon atom can be substituted with a nitrogen, sulfur or oxygen atom; more preferably $R^{19}$ is a linear or branched, $C_1$-$C_{20}$-alkyl radical; more preferably $R^{19}$ is a methyl or ethyl radical; examples of group $C(R^{19})_2R^{18}$ are tert-butyl, isopropyl, cyclopentyl, cyclohexyl, 2 furanyl radicals;

A preferred class of the compounds of formula (I) is represented by formula (IIa):

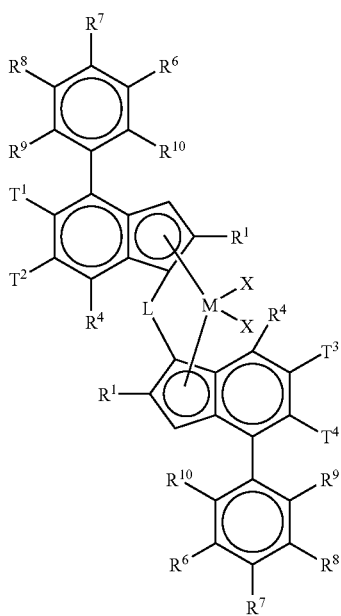

(IIa)

Wherein M, L, X, $T^1$, $T^2$, $T^3$, $T^4$, $R^1$, $R^4$, $R^6$, $R^7$, $R^8$, $R^9$ and $R^{10}$ have the meaning reported above.

A further preferred class of compounds of formula (I) has formula (IIb)

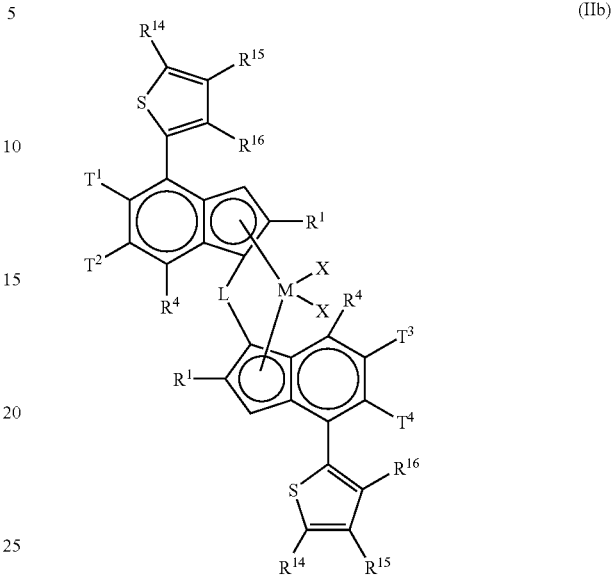

(IIb)

Wherein M, L, X, $T^1$, $T^2$, $T^3$, $T^4$, $R^1$, $R^4$, $R^{14}$, $R^{15}$, $R^{16}$ have the meaning reported above.

In a further preferred embodiment $T^1$ is equal to $T^4$ and $T^2$ is equal to $T^3$.

Examples of compounds having formula (I) are as follows
racemic-Me$_2$Si(2-methyl-4-phenyl-5-methoxy-6-methylinden-1-yl)$_2$ZrCl$_2$
racemic-Me$_2$Si(2-methyl-4-phenyl-5-methoxy-6-phenylinden-1-yl)$_2$ZrCl$_2$
racemic-Me$_2$Si(2-methyl-4-phenyl-5-methoxy-6-isopropylinden-1-yl)$_2$ZrCl$_2$
racemic-Me$_2$Si(2-methyl-4-phenyl-5-methoxy-6-cyclohexylinden-1-yl)$_2$ZrCl$_2$
racemic-Me$_2$Si(2-methyl-4-phenyl-5-methoxy-6-tert-butylinden-1-yl)$_2$ZrCl$_2$
racemic-Me$_2$Si(2-methyl-4-(thiophen-2-yl)-5-methoxy-6-tert-butylinden-1-yl)$_2$ZrCl$_2$
racemic-Me$_2$Si(2-methyl-4-(5-methylthiophen-2-yl)-5-methoxy-6-tert-butylinden-1-yl)$_2$ZrCl$_2$
racemic-Me$_2$Si(2-methyl-4-(benzothiophen-2-yl)-5-methoxy-6-tert-butylinden-1-yl)$_2$ZrCl$_2$
racemic-Me$_2$Si(2-methyl-4-(benzothiophen-2-yl)-5-methoxy-6-tert-butylinden-1-yl)$_2$ZrCl$_2$
racemic-Me$_2$Si(2-methyl-4-(4-pyridyl)-5-methoxy-6-tert-butylinden-1-yl)$_2$ZrCl$_2$
racemic-Me$_2$Si(2-methyl-4-(tert-butylphenyl)-5-methoxy-6-tert-butylinden-1-yl)$_2$ZrCl$_2$
racemic-Me$_2$Si(2-methyl-4-(tert-butylphenyl)-5-ethoxy-6-tert-butylinden-1-yl)$_2$ZrCl$_2$
racemic-Me$_2$Si(2-methyl-4-(2,5-dimethylphenyl)-5-methoxy-6-tert-butylinden-1-yl)$_2$ZrCl$_2$
racemic-Me$_2$Si(2-ethyl-4-phenyl-5-methoxy-6-tert-butylinden-1-yl)$_2$ZrCl$_2$
racemic-Me$_2$Si(2-propyl-4-phenyl-5-methoxy-6-tert-butylinden-1-yl)$_2$ZrCl$_2$
racemic-anti-Me$_2$Si(2-methyl-4-phenyl-5-methoxy-6-tert-butylinden-1-yl)(2-methyl-4-(5-methylthiophen-2-yl)-5-methoxy-6-tert-butylinden-1-yl)ZrCl$_2$ racemic-anti-Me₂Si(2-methyl-4-phenyl-5-methoxy-6-tert-butylinden-1-yl)(2-methyl-4-(5-methylthiophen-2-yl)-5-ethoxy-6-tert-butylinden-1-yl)ZrCl₂ and their correspondent dimethyl derivatives and further the corresponding titanium, and hafnium compounds.

Preferably the metallocene compounds object of the present invention are in their racemic(rac) or anti-racemic form.

For the purpose of the present invention the term "racemic (rac) form" means that the same substituents on the two cyclopentadienyl moieties are on the opposite side with respect to the plane containing the zirconium and the centre of the said cyclopentadienyl moieties. "anti-racemic form" means that the bulkier substituents of the two cyclopentadienyl moieties on the metallocene compound are on the opposite side with respect to the plane containing the zirconium and the centre of the said cyclopentadienyl moieties as shown in the following compound:

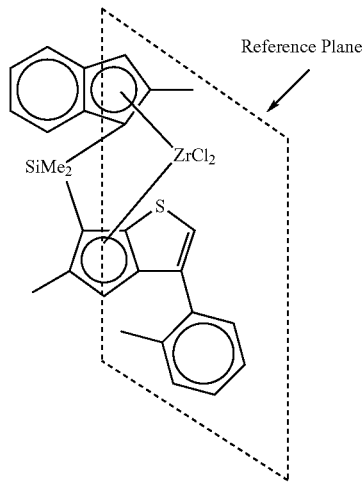

A further object of the present invention is a catalyst system for the polymerization of olefin obtainable by contacting:

a) a metallocene compound of formula (I);

b) at least an alumoxane or a compound able to form an alkylmetallocene cation; and c) optionally an organo aluminum compound.

Preferably the metallocene compounds have formulas selected from (Ia), (IIa) or (IIb).

Alumoxanes used as component b) in the catalyst system according to the present invention can be obtained by reacting water with an organo-aluminium compound of formula $H_jAlU_{3-j}$ or $H_jAl_2U_{6-j}$, where the U substituents, same or different, are hydrogen atoms, halogen atoms, $C_1$-$C_{20}$-alkyl, $C_3$-$C_{20}$-cyclalkyl, $C_6$-$C_{20}$-aryl, $C_7$-$C_{20}$-alkylaryl or $C_7$-$C_{20}$-arylalkyl radicals, optionally containing silicon or germanium atoms, with the proviso that at least one U is different from halogen, and j ranges from 0 to 1, being also a non-integer number. In this reaction the molar ratio of Al/water is preferably comprised between 1:1 and 100:1.

The alumoxanes used in the catalyst system according to the invention are considered to be linear, branched or cyclic compounds containing at least one group of the type:

wherein the substituents U, same or different, are defined above.

In particular, alumoxanes of the formula:

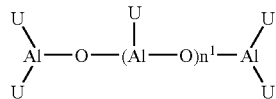

can be used in the case of linear compounds, wherein $n^1$ is 0 or an integer of from 1 to 40 and the substituents U are defined as above; or alumoxanes of the formula:

can be used in the case of cyclic compounds, wherein $n^2$ is an integer from 2 to 40 and the U substituents are defined as above.

Examples of alumoxanes suitable for use according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those described in WO 99/21899 and in WO01/21674 in which the alkyl and aryl groups have specific branched patterns.

Non-limiting examples of aluminium compounds that can be reacted with water to give suitable alumoxanes (b), described in WO 99/21899 and WO01/21674, are:

tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluoro-phenyl)-propyl]aluminium, tris[2-(4-chloro-phenyl)-propyl]aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl)aluminium, tris[2-(pentafluorophenyl)-propyl]aluminium, tris[2,2-diphenyl-ethyl]aluminium and tris[2-phenyl-2-methyl-propyl]aluminium, as well as the corresponding compounds wherein one of the hydrocarbyl groups is replaced with a hydrogen atom, and those wherein one or two of the hydrocarbyl groups are replaced with an isobutyl group.

Amongst the above aluminium compounds, trimethylaluminium (TMA), triisobutylaluminium (TIBA), tris(2,4,4-trimethyl-pentyl)aluminium (TIOA), tris(2,3-dimethylbutyl) aluminium (TDMBA) and tris(2,3,3-trimethylbutyl) aluminium (TTMBA) are preferred.

Non-limiting examples of compounds able to form an alkylmetallocene cation are compounds of formula $D^+E^-$, wherein $D^+$ is a Brønsted acid, able to donate a proton and to react irreversibly with a substituent X of the metallocene of formula (I) and $E^-$ is a compatible anion, which is able to stabilize the active catalytic species originating from the reaction of the two compounds, and which is sufficiently labile to be removed by an olefinic monomer. Preferably, the anion $E^-$ comprises one or more boron atoms. More preferably, the anion $E^-$ is an anion of the formula $BAr_4^{(-)}$, wherein the substituents Ar which can be identical or different are aryl radicals such as phenyl, pentafluorophenyl or bis(trifluoromethyl)phenyl. Tetrakis-pentafluorophenyl borate is particularly preferred compound, as described in WO 91/02012. Moreover, compounds of formula $BAr_3$ can be conveniently used. Compounds of this type are described, for example, in the International patent application WO 92/00333. Other examples of compounds able to form an alkylmetallocene cation are compounds of formula $BAr_3P$ wherein P is a substituted or unsubstituted pyrrol radical. These compounds are described in WO01/62764. Compounds containing boron atoms can be conveniently supported according to the description of DE-A-19962814 and DE-A-19962910. All these compounds containing boron atoms can be used in a molar ratio between boron and the metal of the metallocene comprised between about 1:1 and about 10:1; preferably 1:1 and 2.1; more preferably about 1:1.

Non limiting examples of compounds of formula $D^+E^-$ are:
Tributylammonium tetrakis(pentafluorophenyl)borate,
Tributylammonium tetrakis(pentafluorophenyl)aluminate,
Tributylammonium tetrakis(trifluoromethylphenyl)borate,
Tributylammonium tetrakis(4-fluorophenyl)borate,
Dimethylbenzylammonium-tetrakis(pentafluorophenyl)borate,
Dimethylhexylammonium-tetrakis(pentafluorophenyl)borate,
N,N-Dimethylanilinium tetrakis(pentafluorophenyl)borate,
N,N-Dimethylanilinium tetrakis(pentafluorophenyl)aluminate,
Dimethylbenzylammonium-tetrakis(pentafluorophenyl)borate,
Dimethylhexylammonium-tetrakis(pentafluorophenyl)borate,
Di(cyclohexyl)ammonium tetrakis(pentafluorophenyl)borate,
Triphenylcarbenium tetrakis(pentafluorophenyl)borate,
Triphenylcarbenium tetrakis(pentafluorophenyl)aluminate,
Ferrocenium tetrakis(pentafluorophenyl)borate,
Ferrocenium tetrakis(pentafluorophenyl)aluminate.

Organic aluminum compounds used as compound c) are those of formula $H_jAlU_{3-j}$ or $H_jAl_2U_{6-j}$ as described above.

The catalysts of the present invention can also be supported on an inert carrier. This is achieved by depositing the metallocene compound a) or the product of the reaction thereof with the component b), or the component b) and then the metallocene compound a) on an inert support. The support can be a porous solid such as talc, a sheet silicate, an inorganic oxide or a finely divided polymer powder (e.g. polyolefin). Suitable inorganic oxides may be found among the oxides of elements of groups 2, 3, 4, 5, 13, 14, 15 and 16 of the Periodic Table of the Elements. Examples of oxides preferred as supports include silicon dioxide, aluminum oxide, and also mixed oxides of the elements calcium, aluminum, silicon, magnesium or titanium and also corresponding oxide mixtures, magnesium halides, styrene/divinylbenzene copolymers, polyethylene or polypropylene. Other inorganic oxides which can be used alone or in combination with the above-mentioned preferred oxidic supports are, for example, MgO, $ZrO_2$, $TiO_2$ or $B_2O_3$.

A suitable class of supports which can be used is that constituted by porous organic supports functionalized with groups having active hydrogen atoms. Particularly suitable are those in which the organic support is a partially crosslinked styrene polymer. Supports of this type are described in European application EP-633 272.

Another class of inert supports particularly suitable for use according to the invention is that of polyolefin porous prepolymers, particularly polyethylene.

A further suitable class of inert supports for use according to the invention is that of porous magnesium halides such as those described in International application WO 95/32995.

The support materials used preferably have a specific surface area in the range from 10 to 1000 $m^2/g$, a pore volume in the range from 0.1 to 5 ml/g and a mean particle size of from 1 to 500 μm. Preference is given to supports having a specific surface area in the range from 50 to 500 $m^2/g$, a pore volume in the range from 0.5 to 3.5 ml/g and a mean particle size in the range from 5 to 350 μm. Particular preference is given to supports having a specific surface area in the range from 200 to 400 $m^2/g$, a pore volume in the range from 0.8 to 3.0 ml/g and a mean particle size of from 10 to 300 μm.

The inorganic support can be subjected to a thermal treatment, e.g. to remove adsorbed water. Such a drying treatment is generally carried out at from 80 to 300° C., preferably from 100 to 200° C., with drying at from 100 to 200° C. preferably being carried out under reduced pressure and/or a blanket of inert gas (e.g. nitrogen), or the inorganic support can be calcined at from 200 to 1000° C. to produce the desired structure of the solid and/or set the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090.

The inorganic support material can also be chemically modified. For example, treatment of silica gel with $(NH_4)_2SiF_6$ leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by means of appropriate purification and drying operations before use. It is also possible to use functionalized polymer supports, e.g. supports based on polystyrene, via whose functional groups, for example ammonium or hydroxy groups, at least one of the catalyst components can be immobilized. The solid compound obtained by supporting the catalyst system object of the present invention on a carrier in combination with the further addition of the alkylaluminium compound either as such or preracted with water if necessary, can be usefully employed in the gas-phase or slurry polymerization.

The catalyst system of the present invention can be used also in a solution polymerization process.

For the purpose of the present invention the term solution polymerization means preferably that the polymer is fully soluble in the polymerization medium at the polymerization temperature used, and in a concentration range of at least 5% by weight; more preferably from 5 to 50% by weight.

In order to have the polymer completely soluble in the polymerization medium, a mixtures of monomers for copolymers or only one monomer for homopolymers in the presence of an inert solvent can be used. This solvent can be an aliphatic or cycloaliphatic hydrocarbon such as butane, hexane, heptane isooctane, cyclohexane and methylcyclohexane. It is also possible to use mineral spirit or a hydrogenated diesel oil fraction. Also aromatic hydrocarbons can be used such as toluene. Preferred solvents to be used are cyclohexane and methylcyclohexane. In case propylene is used as monomer for the obtainment of propylene copolymers in solution polymerization process, the propylene content in the liquid phase of the polymerization medium preferably ranges from 5% to 60% by weight; more preferably from 20% to 50% by weight.

The catalyst system comprising the metallocene compound of formula (I) can be used for polymerizing olefins, in particular alpha-olefins in high yields to obtain polymers having high molecular weight. Therefore a further object of the present invention is a process for preparing a alpha-olefin polymer comprising contacting under polymerization conditions one or more alpha-olefins of formula $CH_2=CHA$ wherein A is hydrogen or a $C_1$-$C_{20}$ alkyl radical, in the presence of a catalyst system as described above.

Non limitative examples of alpha-olefins of formula $CH_2=CHA$ are: ethylene, propylene, 1-butene, 1-hexene, 1-octene and 4-methyl-1-pentene, preferred alpha olefins are ethylene, propylene and 1-butene.

The metallocene compounds of formula (I) object of the present invention are particularly suitable for the homo and copolymerization of propylene. In fact, the metallocene-based catalyst system of the present invention when used for homo or copolymerizing propylene are able to give polymers having a high molecular weight in high yields also at high temperatures rendering thus possible to use it in the industrial plants that use polymerization temperatures higher than 50° C. and that can be comprised between 60° and 200° C., preferably between 60° C. and 120° C.

As said above, the metallocene compounds of formula (I) are particularly suitable for the copolymerization of propylene, therefore a further object of the present invention is a process for the preparation of propylene copolymers comprising the step of contacting, under polymerization conditions, propylene with ethylene or one or more alpha olefins of formula $CH_2=CHA^1$, wherein $A^1$ is a $C_2$-$C_{20}$ alkyl radical, in the presence of a catalyst system described above. This process is preferably carried out in solution as described above.

Examples of alpha olefins of formula $CH_2=CHA^1$ are 1-butene, 1-hexene, 1-octene and 4-methyl-1-pentene; preferred alpha olefins are ethylene and 1-butene; more preferred alpha olefin is ethylene. The content of alpha-olefins derived units in the propylene copolymer object of the present invention ranges from 0.1 to 90% by mol; preferably it ranges from 5% by mol to 70% by mol; more preferably it ranges from 10% by mol to 60% by mol.

The metallocene compounds of the present invention are also particularly suitable for the preparation of copolymers of ethylene and higher alpha olefins, such as propylene, 1-butene, 1-hexene, 1-octene. The copolymers have a comonomer content ranging from 5 to 50% by mol. Particularly preferred are ethylene/1-butene copolymer having a content of 1-butene derive units ranging from 5 to 50% by mol. Said copolymers can be obtained in high yields by using a gas phase process such a fluidized bed or stirred bed reactor.

As explained above the process for the polymerization of olefins according to the invention can be carried out in the liquid phase in the presence or absence of an inert hydrocarbon solvent, such as in in slurry, or in the gas phase. The hydrocarbon solvent can either be aromatic such as toluene, or aliphatic such as propane, hexane, heptane, isobutane or cyclohexane.

As a general rule, the polymerization temperature is generally comprised between −100° C. and +200° C. and, particularly between 10° C. and +100° C. The polymerization pressure is generally comprised between 0.5 and 100 bar.

The lower the polymerization temperature, the higher are the resulting molecular weights of the polymers obtained.

The polymerization yields depend on the purity of the metallocene compound of the catalyst. The metallocene compounds obtained by the process of the invention can therefore be used as such or can be subjected to purification treatments.

In view of the optimum behavior of the metallocene compounds of formula (I) when used for the homo and copolymerization of propylene, the catalyst system based on the metallocene compounds object of the present invention can be used in a multistage process for preparing heterophasic propylene copolymers. Therefore a further object of the present invention is a multistage polymerization process comprising the following steps:

a) polymerizing propylene with optionally ethylene or one or more alpha olefins of formula $CH_2=CHA^1$, wherein $A^1$ is a $C_2$-$C_{20}$ alkyl radical, in the presence of a catalysts system described above;

b) contacting, under polymerization conditions, propylene with ethylene or one or more alpha olefins of formula $CH_2=CHA^1$, and optionally with a non-conjugated diene, in the presence of the polymer obtained in step a) and optionally in the presence of an additional organo aluminum compound;

provided that the polymer produced in step a) is different from the copolymer produced in step b) for the comonomer derived units amount or comonomer derived units structure;

wherein the amount of the polymer obtained in step a) ranges from 2% to 98% by weight of the polymer obtained in the whole process and the amount of polymer obtained in step b) ranges from 98% to 2% by weight of the polymer obtained in the whole process.

Preferably step a) further comprises a prepolymerization step a-1).

The prepolymerization step a-1) can be carried out by contacting the catalyst system described above with one or more alpha olefins of formula $CH^2=CHA$ wherein A is hydrogen or a $C_1$-$C_{20}$ alkyl radical; preferably said alpha olefin is propylene or ethylene, at a temperature ranging from −20° C. to 70° C., in order to obtain a prepolymerized catalyst system containing preferably from 5 to 500 g of polymer per gram of catalyst system.

Step a) of the present invention can be carried out in liquid phase, in which the polymerization medium can be an inert hydrocarbon solvent or the polymerization medium can be liquid propylene optionally in the presence of an inert hydrocarbon solvent, and of ethylene or one or more comonomer of formula $CH_2=CHA^1$, or step a) can be carried out in a gas phase. Said hydrocarbon solvent can be either aromatic (such as toluene) or aliphatic (such as propane, hexane, heptane, isobutane, cyclohexane and 2,2,4-trimethylpentane).

Preferably the polymerization medium is liquid propylene. It can optionally contains minor amounts (up to 20% by weight, preferably up to 10% by weight, more preferably up to 5% by weight) of an inert hydrocarbon solvent or of ethylene or one or more comonomer of formula $CH_2=CHA^1$.

Step a) can be carried out in the presence of hydrogen. The amount of hydrogen present during the polymerization reaction is preferably more than 1 ppm; more preferably from 5 to 2000 ppm; even more preferably from 6 to 500 ppm with respect to the propylene present in the reactor. Hydrogen can be added either at the beginning of the polymerization reaction or it can also be added at a later stage after a prepolymerization step has been carried out.

The propylene polymer obtained in step a) is a propylene homopolymer or a propylene copolymer containing up to 20% by mol preferably from 0.1 to 10% by mol, more preferably from 1% to 5% by mol of derived units of ethylene or one or more alpha olefins of formula $CH_2=CHA^1$. Preferred comonomers are ethylene or 1-butene. Preferably in step a) a propylene homopolymer is produced. The content of the polymer obtained in step a) preferably ranges from 5% to 90% by weight of the polymer produced in the whole process, more preferably it ranges from 10% to 70% by weight and still more preferably from 25% to 65% by weight of the total polymer produced in the whole process.

Step b) can be carried out in liquid phase, in which the polymerization medium can be an inert hydrocarbon solvent or the polymerization medium can be liquid propylene optionally in the presence of an inert hydrocarbon solvent, and of ethylene or one or more comonomer of formula $CH_2=CHA^1$, or step a) can be carried out in a gas phase. Preferably step b) is carried out in a gas phase, preferably in a fluidized or stirred bed reactor. The polymerization temperature is generally comprised between $-100°$ C. and $+200°$ C., and, preferably, between $10°$ C. and $+90°$ C. The polymerization pressure is generally comprised between 0.5 and 100 bar.

In step b) a propylene copolymer containing from 5% to 90% by mol, preferably from 10% to 50% by mol, more preferably from 15% to 30% by mol of derived units of ethylene or one or more alpha olefins of formula $CH_2=CHA^1$ is produced. Examples of comonomer of formula $CH_2=CHA^1$ that can be used in step b) of the present invention are: 1-butene, 1-pentene, 4-methyl-1-pentene, 1-hexene, 1-octene, 4,6-dimethyl-1-heptene, 1-decene, 1-dodecene, 1-tetradecene, 1-hexadecene, 1-octadecene and 1-eicosene. Preferred comonomers are ethylene or 1-butene.

The content of polymer obtained in step b) preferably ranges from 10 to 95% by weight of the polymer produced in the whole process, preferably it ranges from 30% to 90% by weight and more preferably from 35% to 75% by weight.

The polymer obtained in step b) can optionally contains up to 20% by mol of a non conjugated diene. Non conjugated dienes can be a straight chain, branched chain or cyclic hydrocarbon diene having from 6 to 20 carbon atoms. Examples of suitable non-conjugated dienes are:

straight chain acyclic dienes, such as 1,4-hexadiene and 1,6-octadiene;

branched chain acyclic dienes, such as 5-methyl-1,4-hexadiene, 3,7-dimethyl-1,6-octadiene, 3,7-dimethyl-1,7-octadiene and mixed isomers of dihydro myricene and dihydroocinene;

single ring alicyclic dienes, such as 1,3-cyclopentadiene, 1,4-cyclohexadiene, 1,5-cyclooctadiene and 1,5-cyclododecadiene;

multi-ring alicyclic fused and bridged ring dienes, such as tetrahydroindene, methyl tetrahydroindene, dicyclopentadiene, bicyclo-(2,2,1)-hepta-2,5-diene; and alkenyl, alkylidene, cycloalkenyl and cycloalkylidene norbornenes, such as 5-methylene-2-norbornene (MNB), 5-propenyl-2-norbornene, 5-isopropylidene-2-norbornene, 5-(4-cyclopentenyl)-2-norbornene, 5-cyclohexylidene-2-norbornene, 5-vinyl-2-norbornene and norbornadiene.

Preferred dienes are 1,4-hexadiene (HD), 5-ethylidene-2-norbornene (ENB), 5-vinylidene-2-norbornene (VNB), 5-methylene-2-norbornene (MNB) and dicyclopentadiene (DCPD). Particularly preferred dienes are 5-ethylidene-2-norbornene (ENB) and 1,4-hexadiene (HD).

When present the non-conjugated dienes are preferably incorporated into the polymer in an amount from 0.1% to about 20% by mol, preferably from 0.5% to 15% by mol, and more preferably from 0.5% to 7% by mol. If desired, more than one diene may be incorporated simultaneously, for example HD and ENB, with total diene incorporation within the limits specified above.

A further multistage polymerization process comprises the following steps:

a1) polymerizing propylene with optionally ethylene or one or more monomers selected from alpha olefins of formula $CH_2=CHA^1$, wherein $A^1$ is a $C_2$-$C_{20}$ alkyl radical, in the presence of a catalysts system described above;

b1) contacting, under polymerization conditions, ethylene with propylene or one or more alpha olefins of formula $CH_2=CHA^1$, and optionally with a non-conjugated diene, in the presence of the polymer obtained in step a) and optionally in the presence of an additional organo aluminum compound;

provided that the polymer produced in step a1) is different from the copolymer produced in step b1) for the comonomer derived units amount or comonomer derived units structure;

wherein the amount of the polymer obtained in step a1) ranges from 2% to 98% by weight of the polymer obtained in the whole process and the amount of polymer obtained in step b1) is ranges from 98% to 2% by weight of the polymer obtained in the whole process.

Preferably step a1) further comprises a prepolymerization step a1-1).

The prepolymerization step a1-1) can be carried out by contacting the catalyst system described above with one or more alpha olefins of formula $CH^2=CHA$ wherein A is hydrogen or a $C_1$-$C_{20}$ alkyl radical; preferably said alpha olefin is propylene or ethylene, at a temperature ranging from $-20°$ C. to $70°$ C., in order to obtain a prepolymerized catalyst system containing preferably from 5 to 500 g of polymer per gram of catalyst system.

Step a1) can be carried out in liquid phase, in which the polymerization medium can be an inert hydrocarbon solvent or the polymerization medium can be liquid propylene optionally in the presence of an inert hydrocarbon solvent, and ethylene or one or more comonomer of formula $CH_2=CHA^1$, or step a1) can be carried out in a gas phase. Said hydrocarbon solvent can be either aromatic (such as toluene) or aliphatic (such as propane, hexane, heptane, isobutane, cyclohexane and 2,2,4-trimethylpentane). Preferably the polymerization medium is liquid propylene. It can optionally contains minor amounts (up to 20% by weight, preferably up to 10% by weight, more preferably up to 5% by weight) of an inert hydrocarbon solvent or of ethylene or one or more comonomer of formula $CH_2=CHA^1$.

Step a1) can be carried out in the presence of hydrogen. The amount of hydrogen present during the polymerization reaction is preferably more than 1 ppm; more preferably from 5 to 2000 ppm; even more preferably from 6 to 500 ppm with respect to the propylene present in the reactor. Hydrogen can be added either at the beginning of the polymerization reaction or it can also be added at a later stage after a prepolymerization step has been carried out.

The propylene polymer obtained in step a1) is a propylene homopolymer or a propylene copolymer containing up to 20% by mol preferably from 0.1 to 10% by mol, more preferably from 1% to 5% by mol of derived units of ethylene or one or more alpha olefins of formula $CH_2=CHA^1$. Preferred comonomers are ethylene or 1-butene. Preferably in step a1) a propylene homopolymer is produced. The content of the polymer obtained in step a1) preferably ranges from 5% to 90% by weight of the polymer produced in the whole process, more preferably it ranges from 10% to 70% by weight and still more preferably from 25% to 65% by weight of the total polymer produced in the whole process.

Step b1) can be carried out in liquid phase, in which the polymerization medium can be an inert hydrocarbon solvent or the polymerization medium can be a liquid monomer such as ethylene, propylene or one or more comonomer of formula $CH_2=CHA^1$ optionally in the presence of an inert hydrocarbon solvent, or step b1) can be carried out in a gas phase. Preferably step b1) is carried out in a gas phase, preferably in a fluidized or stirred bed reactor. The polymerization temperature is generally comprised between $-100°$ C. and $+200°$ C., and, preferably, between $10°$ C. and $+90°$ C. The polymerization pressure is generally comprised between 0.5 and 100 bar.

In step b1) an ethylene copolymer containing from 5% to 90% by mol, preferably from 10% to 50% by mol, more preferably from 15% to 30% by mol of derived units of propylene or one or more alpha olefins of formula $CH_2=CHA^1$ is produced. Examples of comonomer of formula $CH_2=CHA^1$ that can be used in step b1) of the present invention are: 1-butene, 1-pentene, 4-methyl-1-pentene, 1-hexene, 1-octene, 4,6-dimethyl-1-heptene, 1-decene, 1-dodecene, 1-tetradecene, 1-hexadecene, 1-octadecene and 1-eicosene. Preferred comonomers are propylene or 1-butene.

The content of polymer obtained in step b1) preferably ranges from 10 to 95% by weight of the polymer produced in the whole process, preferably it ranges from 30% to 90% by weight and more preferably from 35% to 75% by weight.

The polymer obtained in step b1) can optionally contains up to 20% by mol of a non conjugated diene. Non conjugated dienes can be a straight chain, branched chain or cyclic hydrocarbon diene having from 6 to 20 carbon atoms. Examples of suitable non-conjugated dienes are:
  straight chain acyclic dienes, such as 1,4-hexadiene and 1,6-octadiene;
  branched chain acyclic dienes, such as 5-methyl-1,4-hexadiene, 3,7-dimethyl-1,6-octadiene, 3,7-dimethyl-1,7-octadiene and mixed isomers of dihydro myricene and dihydroocinene;
  single ring alicyclic dienes, such as 1,3-cyclopentadiene, 1,4-cyclohexadiene, 1,5-cyclooctadiene and 1,5-cyclododecadiene;
  multi-ring alicyclic fused and bridged ring dienes, such as tetrahydroindene, methyl tetrahydroindene, dicyclopentadiene, bicyclo-(2,2,1)-hepta-2,5-diene; and
  alkenyl, alkylidene, cycloalkenyl and cycloalkylidene norbornenes, such as 5-methylene-2-norbornene (MNB), 5-propenyl-2-norbornene, 5-isopropylidene-2-norbornene, 5-(4-cyclopentenyl)-2-norbornene, 5-cyclohexylidene-2-norbornene, 5-vinyl-2-norbornene and norbornadiene.

Preferred dienes are 1,4-hexadiene (HD), 5-ethylidene-2-norbornene (ENB), 5-vinylidene-2-norbornene (VNB), 5-methylene-2-norbornene (MNB) and dicyclopentadiene (DCPD). Particularly preferred dienes are 5-ethylidene-2-norbornene (ENB) and 1,4-hexadiene (HD).

When present the non-conjugated dienes are preferably incorporated into the polymer in an amount from 0.1% to about 20% by mol, preferably from 0.5% to 15% by mol, and more preferably from 0.5% to 7% by mol. If desired, more than one diene may be incorporated simultaneously, for example HD and ENB, with total diene incorporation within the limits specified above.

The processes of the present invention can be carried out in one reactor or in two or more reactors in series.

The metallocene compounds object of the present in invention are especially suitable as catalyst component for the production of propylene/higher alpha olefins copolymers having a high molecular weight in high yields.

Therefore a further object of the present invention is a process for preparing a polymer containing from 99% by mol to 50% by mol of derived units of propylene and from 1% by mol to 50% by mol of derived units of one or more alpha olefins of formula $CH_2=CHW$ wherein W is a $C_2$-$C_{10}$ hydrocarbon radical comprising contacting under polymerization conditions propylene and one or more alpha olefins of formula $CH_2=CHW$ in the presence of a catalyst system obtainable by contacting:
  a) a metallocene compound of formula (I) as described above
  b) an alumoxane or a compound capable of forming an alkyl metallocene cation; and optionally
  c) an organo aluminum compound.

Said polymerization process can be carried out in liquid phase, preferably in the presence of an inert hydrocarbon solvent. Said hydrocarbon solvent can be either aromatic (such as toluene) or aliphatic (such as hexane, heptane, isobutane, cyclohexane, isododecane and 2,2,4-trimethylpentane). Optionally the polymerization process of the present invention can be carried out by using a mixture of propylene and the alpha olefin of formula $CH_2=CHW$ wherein W is a $C_2$-$C_{10}$ hydrocarbon radical such as 1-butene, 1-hexene or 1-octene as polymerization medium.

Preferably the polymerization medium is an aliphatic solvent such as ciclohexane or isododecane or a mixture of high boiling aliphatic hydrocarbons such as for example ISOPAR® series of solvent.

Preferably the process of the present invention is carried out under condition so that the polymer is dissolved in the polymerization medium.

The polymerization temperature preferably ranges from 0° C. to 250° C.; more preferably it is comprised between 20° C. and 150° C. and, more particularly the polymerization temperature is between 60° C. and 120° C.; even more particularly the temperature is between 75° C. and 120° C., this allows to carry out the polymerization at high temperature in order to reduce the energy required for solvent recycling. The catalyst of the present invention allows to obtain under these conditions a polymer having still high molecular weight.

Examples of alpha olefins of formula $CH_2$=CHW wherein W is a $C_2$-$C_{10}$ hydrocarbon radical are 1-butene, 1-pentene; 1-hexene; 1-octene and 1-decene. Preferably 1-butene, 1-hexene and 1-octene are used; more preferably 1-butene is used.

The content of alpha olefin of formula $CH_2$=CHW derived units of the copolymer obtained with the process of the present invention ranges preferably from 40% by mol to 3% by mol; preferably it ranges from 35% by mol to 5% by mol. The propylene derived units content of said copolymer ranges preferably from 60% by mol to 97% by mol; more preferably it ranges from 65% by mol to 95% by mol.

Further object of the present invention is a ligand of formula (III)

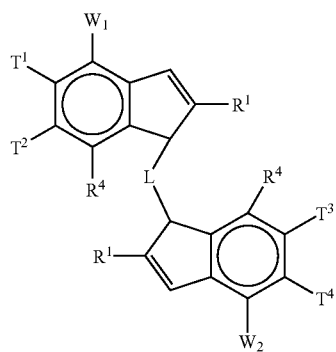

(III)

or its double bond isomers wherein L, $R^1$, $R^4$, $T^1$, $T^2$, $T^3$, $T^4$ and $W^1$, $W^2$ have the meaning reported above.

Preferred ligands have formulas (IIIa) or (IIIb):

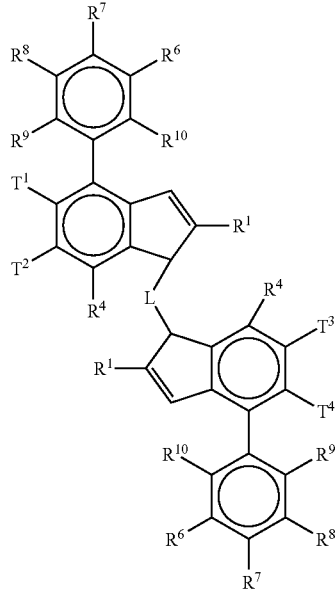

(IIIa)

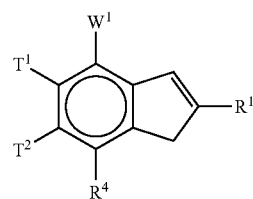

(IIIb)

or their double bond isomers wherein L, n, $R^1$-$R^{18}$ have the meaning reported above.

The metallocene compounds of formula (I) can be obtained with a process comprising the steps of reacting the dianion with a suitable transition metal source such as metal tetrahalide as for example zirconium tetrachloride. The dianion can be obtained for example by the deprotonation of the ligand of formula (III), for example by using an organolithium compound such as buthyl or methyl lithium. The ligand of formula (III) can be easily prepared starting from the cyclopentadienyl moiety of formula (IV)

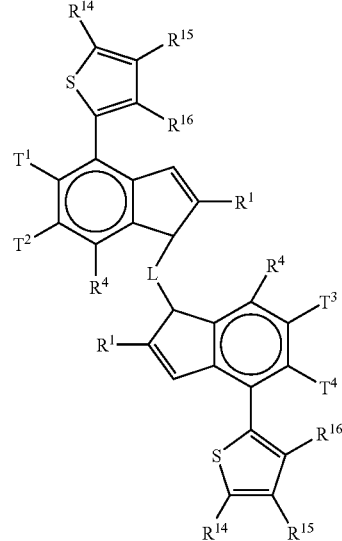

(IV)

wherein $R^1$, $R^2$, $R^3$, $R^4$ and $W^1$ have the meaning described above with a process comprising the following steps:

a) Contacting the compound of formula (IV) and/or its double bond isomers with a base selected from $T^5{}_jB$, $T^5MgT^6$, sodium and potassium hydride, metallic sodium and potassium; wherein $T^5$, j, B and $T^6$ are defined as above, and wherein the molar ratio between said base and the compound of the formula (IV) is at least 1:1; excess of said base can be used;

b) contacting the anionic compound obtained in step a) with a compound of formula $LY^2$ wherein L is defined as above and Y is chlorine, bromine and iodine, preferably Y is chlorine or bromine; to form a compound of formula (IVa)

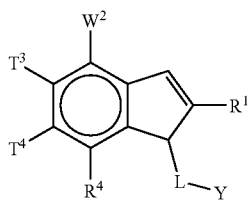

(IVa)

c) contacting the compound of formula (IVa) with the anionic derivative of compound of formula (IV) obtained as described in step a).

When the two indenyl moiety are the same the process described above can be carried out also "one pot" by reacting a calculate amount of the compound of formula $LY_2$ with the dianionic derivative formed in step a).

The above processes are preferably carried out in an aprotic solvent, either polar or apolar. Said aprotic solvent is preferably an aromatic or aliphatic hydrocarbon, optionally halogenated, or an ether; more preferably it is selected from benzene, toluene, pentane, hexane, heptane, cyclohexane, dichloromethane, diethylether, tetrahydrofurane and mixtures thereof. The above process is carried out at a temperature ranging from −100° C. to +80° C., more preferably from −20° C. to +70° C.

The following examples are given to illustrate and not to limit the invention.

EXAMPLES

General Characterization

Intrinsic Viscosity (IV) in Tetrahydronaphthalene

The measurement were done in tetrahydronaphthalene (THN) solution obtained by dissolving the polymer at 135° C. for 1 hour.

Melting Temperature ($T_m$)

Calorimetric measurements were performed by using a differential scanning calorimeter DSC Mettler. The instrument is calibrated with indium and tin standards. The weighted sample (6-8 mg), was sealed into aluminum pans, heated to 200° C. and kept at that temperature for 5 minutes, then cooled at 20° C./min to 5° C., kept 5 minutes at 5° C., then finally heated to 200° C. at a rate of 20° C./min. In this second heating run, the peak temperature was assumed as melting temperature ($T_m$) and the area as the global melting enthalpy (ΔH).

Gel Permeation Chromatography (GPC)

Gel permeation chromatography was carried out at 135° C. in 1,2,4-trichlorobenzene using a GPC apparatus 150 C from Waters.

$^{13}$C-NMR Measurement

The polymer microstructure was investigated by $^{13}$C-NMR analysis. The samples were dissolved with a 8% wt/v concentration in 1,1,2,2-tetrachloroethane-$d_2$ at 120° C. The $^{13}$C-NMR spectra were acquired at 120° C. on a Bruker DPX400 spectrometer operating at 100.61 MHz. In the case of isotactic polypropylene, the mmmm peak at 21.8 ppm was used as internal reference, and the pentad distribution and amounts of regioerrors were determined as described in Resconi, L.; Cavallo, L.; Fait, A.; Piemontesi, F. *Chem. Rev.* 2000, 100, 1253.

In the case of ethylene-propylene copolymers, each spectrum was acquired with a 90° pulse, 12 seconds of delay between pulses and CPD (WALTZ 16) to remove $^1$H-$^{13}$C coupling. About 1500 transients were stored in 32K data points using a spectral window of 6000 Hz.

The assignments of the peaks were made according to Randall[1] and Tritto[2] and the triad distribution and copolymer compositions was determined according to Kakugo. [3]

The $S_{\delta\delta}$ peak at 29.9 ppm (nomenclature according to reference 4) was used as internal reference. The product of reactivity ratios $r_1 \times r_2$ was calculated from the triads according to Carman. [4]

[1] J. C. Randall, Macromol. Chem. Phys. 1989, C29, 201.

[2] I. Tritto, Z. Fan, P. Locatelli, M. Sacchi, I. Camurati, M. Galimberti, Macromolecules 1995, 28, 3342.

[3] M. Kakugo, Y. Naito, K. Mizunuma, T. Miyatake, Macromolecules 1982, 15, 1150.

[4] C. J. Carman, R. A. Harrington, C. E. Wilkes, Macromolecules 1977, 10, 535.

In the case of propylene/butene and propylene/hexene copolymers, each spectrum was acquired with a 90° pulse, 15 seconds of delay between pulses and CPD (WALTZ 16) to remove $^1$H-$^{13}$C coupling. About 1500 transients were stored in 32K data points using a spectral window of 6000 Hz.

The assignments of the resonances were made according to J. C. Randall Macromolecules, 11, 592, (1978) for the propylene-butene copolymers and according to F. Forlini, I. Tritto, P. Locatelli, M. C. Sacchi, F. Piemontesi, Macromol. Chem. Phys., 201, 401-408 (2000) for the propylene-hexene copolymers.

The peak of the Propylene CH was used as internal reference at 28.83 ppm.

The evaluation of diad distribution and the composition was obtained from $S\alpha\alpha$ using the following equations:

$$XX=110S\alpha\alpha(XX)/\Sigma$$

$$XP=100S\alpha\alpha(XP)/\Sigma$$

$$PP=100S\alpha\alpha(PP)/\Sigma$$

Where $\Sigma=\Sigma\ S\alpha\alpha$ and X can be either 1-butene or 1-hexene $$[P]=PP+0.5XP$$

$$[X]=XX+0.5XP$$

Chemicals and Characterization.

All chemicals were handled using standard Schlenk techniques.

Methylalumoxane (MAO) was received from Albemarle as a 30% wt/wt toluene solution and used as such.

Racemic-dimethylsilylbis(2-methyl-4-phenyl-inden-1-yl)dichlorozirconium (C-1) was prepared according to EP 576970;

racemic dimethylsilylbis(2-methyl-4-(4-tert-butylphenyl)-1,5,6,7-tetrahydro-s-indacen-1-yl)dichlorozirconium (C-2)

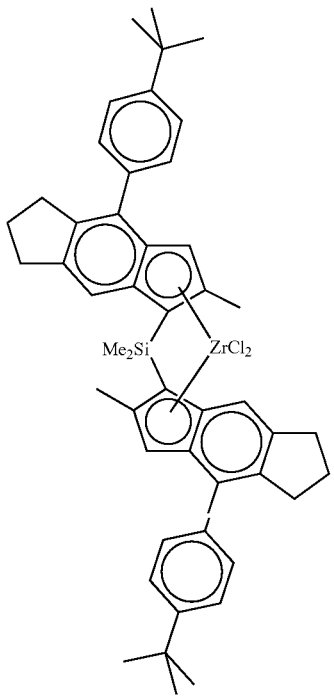

was prepared according to the procedure described in EP05102189.7 Racemic-dimethylsilylbis {η⁵-8-(4-tert-butylphenyl)-6-methyl-5H-indeno[5,6-d][1,3]dioxol-5-yl}dichlorozirconium (C-3)

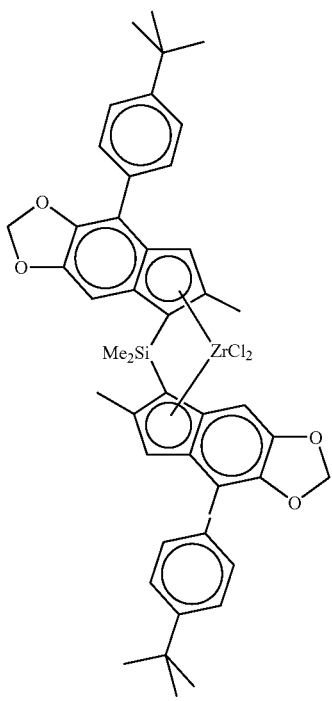

was prepared according to the procedure described in EP 05107248.6

Racemic-dimethylsilylbis(2-methyl-4-(4-tert-butyl-phenyl)-inden-1-yl)dichlorozirconium (C-4) was prepared according to WO 98/40331 (example 65).

Synthesis of racemic dimethylsilylbis(2-methyl-4-phenyl-5-methoxy-6-tert-butylinden-1-yl)dichlorozirconium A-1

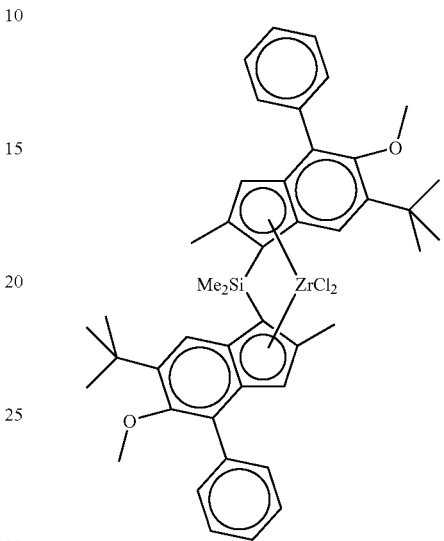

Synthesis of 1-tert-butyl-2-methoxybenzene

Dimethylsulfate (56.7 g, 0.45 mol) was added at room temperature to a well-stirred mixture of 2-tert-butylphenol (45 g, 0.3 mol), $CH_2Cl_2$ (200 ml), 40% aq. NaOH (200 ml) and tetrabutylammonium bromide (1 g). After 16 h of stirring, the organic phase was separated, washed with $H_2O$, dried over $MgSO_4$, evaporated and distilled at 110-112° C./10 Torr. Yield 35 g (71%).

Synthesis of 6-tert-butyl-5-methoxy-2-methyl-1-indanone

A mixture of 1-tert-butyl-2-methoxybenzene (32.8 g, 0.2 mol) and methacrylic acid (21.5 g, 0.25 mol) was added at 60° C. to a well stirred Eaton reagent (55 g $P_2O_5$ and 280 ml of methanesulfonic acid). After 1 h of stirring the reaction mixture was cooled, poured into ice water, and extracted with benzene (3×200 ml). The combined organic layer was washed with water, aq. $NaHCO_3$, dried over $MgSO_4$, evaporated and distilled at 145-150° C./0.7 Torr. Yield 20 g (43%).

$^1$H NMR ($CDCl_3$, 20° C.) δ: 7.66 (s, 1H), 6.86 (s, 1H), 3.91 (s, 3H), 3.29 (q, 1H), 2.64 (m, 2H), 1.35 (s, 9H), 1.26 (d, 3H).

Synthesis of 4-bromo-6-tert-butyl-5-methoxy-2-methyl-1-indanone

Bromine (4.4 ml, 86 mmol) was added at 0° C. to a mixture of 6-tert-butyl-5-methoxy-2-methyl-1-indanone (20 g, 86 mmol), NaOAc (20.4 g) and tetrabutylammonium bromide (0.5 g) in $CH_2Cl_2$ (50 ml) and $H_2O$ (150 ml). After 16 h, 2.5 ml of $Br_2$ and 12 g of NaOAc were added. After 24 h of stirring, the organic phase was separated, washed with water, 10% aq. $Na_2SO_3$, aq. $NaHCO_3$, dried over $MgSO_4$ and evaporated. The residue was used without purification.

$^1$H NMR (CDCl$_3$, 20° C.) δ: 7.71 (s, 1H), 4.03 (s, 31H), 3.31 (q, 1H), 2.72 (m, 1H), 2.61 (dd, 1H), 1.41 (s, 9H), 1.32 (d, 3H).

Synthesis of 5-tert-butyl-6-methoxy-2-methyl-7-phenyl-1H-indene

Pd(OAc)$_2$ (0.6 g, 3 mol %) and PPh$_3$ (1.41 g, 6 mol %) were added to a well stirred mixture of 4-bromo-6-tert-butyl-5-methoxy-2-methyl-1-indanone (28 g, 90 mmol), phenylboronic acid (15.3 g, 126 mmol) and K$_2$CO$_3$ (34.8 g, 249 mmol) in DME (345 mL)/H$_2$O (114 mL). The resulting mixture was refluxed with stirring for 5 h, cooled, poured into water and extracted by CH$_2$Cl$_2$ (3×200 mL). The combined organic phase was washed with aq. Na$_2$CO$_3$, water, dried over MgSO$_4$, evaporated and purified by extraction with hot hexane (3×200 mL). The residue after evaporation was used without purification.

This compound was dissolved in Et$_2$O (30 mL) and added dropwise at 0° C. to LiAlH$_4$ (1.71 g, 45 mmol) in Et$_2$O (300 mL). After 1 h stirring, 5% HCl (150 mL) was added, the organic phase was separated, washed with aq. Na$_2$CO$_3$, dried over MgSO$_4$ and evaporated. The residue was dissolved in benzene (500 mL), p-TSA (1 g) was added, the resulting mixture was refluxed for 10 min, cooled, washed with water, dried over MgSO$_4$, evaporated and distilled in vacuo. Yield=13.5 g (50%), colorless viscous oil.

$^1$H NMR (CDCl$_3$, 20° C.) δ: 7.67-7.54 (m, 5H), 7.39 (s, 1H), 6.60 (s, 1H), 3.38 (s, 3H), 3.28 (s, 2H), 2.21 (s, 3H), 1.61 (s, 9H).

Synthesis of bis(6-tert-butyl-5-methoxy-2-methyl-4-phenyl-1H-inden-1-yl)dimethylsilane A solution of 5-tert-butyl-6-methoxy-2-methyl-7-phenyl-1H-indene (11.20 g, 38.3 mmol) in Et$_2$O (100 mL) was cooled to −40° C., and n-BuLi in hexane (1.6M, 29.34 mL, 38.3 mmol) was added. The resulting mixture was allowed to warm to room temperature, stirred for 3 h, and cooled to −60° C. CuCN (103 mg, 1.15 mmol) and SiMe$_2$Cl$_2$ (2.31 mL, 19.15 mmol) in Et$_2$O (20 mL) were added. The resulting mixture was allowed to warm to room temperature, and stirred for 16 h. H$_2$O (20 mL) and benzene (200 mL) were added, the organic phase was separated, dried over MgSO$_4$, passed through silica gel and evaporated. The residue was dried in vacuo (pale-yellow solid) and used without purification.

$^1$H NMR (CDCl$_3$, 20° C.) δ: 7.56-7.47 (group of m, 10H); 7.40 (s); 7.38 (s) {2H}; {C$_{Ar}$—H}; 6.49 (bs); 6.40 (bs) {2H, —CH=}; 3.63 (s); 3.61 (s) {2H, >CH—}; 3.27 (s, 6H, —OCH$_3$); 2.17 (bs); 2.02 (bs) {6H, —C—CH$_3$}; 1.48 (s); 1.47 (s) {18H, —C(CH$_3$)$_3$}; −0.04 (s); −0.12 (s); −0.13 (s) {6H, Si—CH$_3$}.

Synthesis of racemic dimethylsilylbis(2-methyl-4-phenyl-5-methoxy-6-tert-butylinden-1-yl)dichlorozirconium (A-1)

Bis(6-tert-butyl-5-methoxy-2-methyl-4-phenyl-1H-inden-1-yl)dimethylsilane (12.27 g, 19.15 mmol) was dissolved in Et$_2$O (80 mL), cooled to −40° C., and n-BuLi (1.6M in hexane, 25.7 mL, 41.1 mmol) was added. The reaction mixture was allowed to warm to room temperature, stirred for 3 h, and evaporated. The resulting yellow powder was suspended in pentane (400 mL), cooled to −60° C., and ZrCl$_4$ (5.14 g, 22.07 mmol) was added. After 5 min Et$_2$O (1 mL) was added. The resulting mixture was allowed to warm to room temperature, stirred for additional 16 h, and filtered. The residue was recrystallized from pentane/CH$_2$Cl$_2$ (5:1) yielding the rac-form (2.65 g, 34.6%).

$^1$H NMR (CDCl$_3$, 20° C.) δ: 7.64 (broad, 4H); 7.54 (s, 2H); 7.45 (m, 4H); 7.35 (m, 2H) {C$_{Ar}$—H}; 6.61 (s, 2H, H of C$_5$ ring); 3.43 (s, 6H, —OCH$_3$); 2.19 (s, 6H, C—CH$_3$); 1.41 (s, 18H, —C(CH$_3$)$_3$); 1.32 (s, 6H, Si—CH$_3$).

Synthesis of racemic dimethylsilylbis(2,6-dimethyl-4-(4-tert-butylphenyl)-5-methoxyinden-1-yl)dichlorozirconium (A-2)

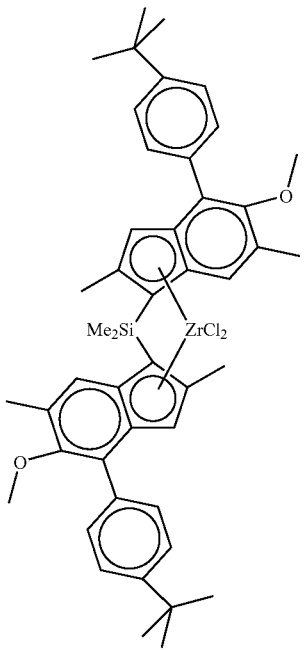

Synthesis of 5-Methoxy-2,6-dimethyl-1-indanone

A mixture of 2-methylanisole (30 g, 0.25 mol) and methacrylic acid (27 g, 0.31 mol) was added at 60° C. to a well stirred Eaton reagent (69 g P$_2$O$_5$ and 350 mL of methanesulfonic acid). After 30 min of stirring the reaction mixture was cooled, poured into ice water, and filtered. The residue was recrystallized from hexane/benzene (10:1). Yield=22 g (46%).

$^1$H NMR (CDCl$_3$, 20° C.) δ: 7.52 (s, 1H), 6.82 (s, 1H), 3.92 (s, 3H), 3.33 (dd, 1H), 2.67 (m, 2H), 2.23 (s, 3H), 1.29 (d, 3H).

Synthesis of 4-Bromo-5-methoxy-2,6-dimethyl-1-indanone

Bromine (6 mL, 11.7 mmol) was added at 0° C. to a mixture of 5-methoxy-2,6-dimethyl-1-indanone (22 g, 11.7 mmol), NaOAc (27 g) and tetrabutylammonium bromide (0.5 g) in CH$_2$Cl$_2$ (100 mL) and H$_2$O (200 mL). After 16 h, 1 mL of Br$_2$ and 6 g of NaOAc were added. After 24 h stirring, the organic phase was separated, washed with water, 10% aq. Na$_2$SO$_3$, aq. NaHCO$_3$, dried over MgSO$_4$ and evaporated. The residue was recrystallized from hexane. Yield=24.7 g (78.4%).

$^1$H NMR (CDCl$_3$, 20° C.) δ: 7.53 (s, 1H), 3.88 (s, 3H), 3.30 (dd, 1H), 2.72 (m, 1H), 2.61 (dd, 1H), 2/73 (s, 3H), 1.32 (d, 3H).

Synthesis of 7-(4-tert-Butylphenyl)-6-methoxy-2,5-dimethyl-1H-indene

Pd(OAc)$_2$ (0.43 g, 3 mol %) and PPh$_3$ (1 g, 6 mol %) were added to a well stirred mixture of 4-bromo-5-methoxy-2,6-dimethyl-1-indanone (17.16 g, 63.8 mmol), tert-butylphenyl-boronic acid (15.9 g, 89 mmol) and K$_2$CO$_3$ (24.6 g, 180 mmol) in DME (240 mL)/H$_2$O (80 mL). The resulting mixture was refluxed with stirring for 5 h, cooled, poured into water and extracted with benzene (3×100 mL). The combined organic phase was washed with aq. Na$_2$CO$_3$, water, dried over MgSO$_4$, and evaporated. The residue was used without purification.

This compound was dissolved in Et$_2$O (200 mL), cooled to 0° C., and LiAlH$_4$ (1.2 g, 32 mmol) was added dropwise. After 3 h stirring, 10% HCl (50 mL) was added, the organic phase was separated, and the water layer was extracted with Et$_2$O (2×50 mL). The combined organic phase was washed with aq. Na$_2$CO$_3$, dried over MgSO$_4$ and evaporated. The residue was dissolved in benzene (200 mL), p-TSA (0.3 g) was added, the resulting mixture was refluxed for 20 min, cooled, washed with water, dried over MgSO$_4$, evaporated and distilled in vacuo. Yield=18.5 g (77%), pale-yellow viscous oil, crystallized within 2 weeks.

$^1$H NMR (CDCl$_3$, 20° C.) δ: 7.46 (m, 4H), 7.10 (s, 1H), 3.40 (s, 3H), 3.21 (s, 2H), 2.40 (s, 3H), 2.12 (s, 3H), 1.43 (s, 9H).

Synthesis of bis[6-(4-tert-butylphenyl)-5-methoxy-2,4-dimethyl-1H-inden-1-yl]dimethylsilane A solution of 7-(4-tert-butylphenyl)-6-methoxy-2,5-dimethyl-1H-indene (6.13 g, 20 mmol) in Et$_2$O (80 mL) was cooled to −40° C., and n-BuLi in hexane (1.6M, 13.13 mL, 21 mmol) was added. The resulting mixture was allowed to warm to room temperature, stirred for 3 h, cooled to −60° C. CuCN (54 mg, 0.6 mmol) and SiMe$_2$Cl$_2$ (1.27 mL, 10.5 mmol) in Et$_2$O (20 mL) were added. The resulting mixture was allowed to warm to room temperature, and stirred for 16 h. H$_2$O (20 mL) and benzene (100 mL) were added, the organic phase was separated, dried over MgSO$_4$, passed through silica gel and evaporated. The residue was dried in vacuo (pale-yellow solid) and used without purification.

$^1$H NMR (CDCl$_3$, 20° C.) δ: 7.62-7.50 (group of m); 7.31 (s); 7.24 (s) {10H, C$_{Ar}$—H}; 6.60 (bs, 2H, —CH=); 3.77 (s); 3.75 (s) {2H, >CH—}; 3.45 (s); 3.44 (s) {6H, —OCH$_3$}; 2.43 (s); 2.42 (s); 2.26 (s); 2.21 (s) {12H, —C—CH$_3$}; 1.47 (s); 1.43 (s) {18H, —C(CH$_3$)$_3$}; −0.14 (s, 6H, Si—CH$_3$).

Synthesis of racemic dimethylsilylbis(2,6-dimethyl-4-(4-tert-butylphenyl)-5-methoxyinden-1-yl)dichlorozirconium (A-2)

The previously obtained bis(6-(4-tert-butylphenyl)-5-methoxy-2,4-dimethyl-1H-inden-1-yl)(dimethyl)silane (10 mmol) was dissolved in Et$_2$O (60 mL), cooled to −40° C., and n-BuLi (1.6M in hexane, 13.1 mL, 21 mmol) was added. The reaction mixture was allowed to warm to room temperature, stirred for 3 h, and evaporated. The resulting powder was suspended in pentane (200 mL), cooled to −60° C., and ZrCl$_4$ (2.45 g, 10.5 mmol) was added. After 5 min Et$_2$O (0.5 mL) was added. The resulting mixture was allowed to warm to room temperature, stirred for additional 16 h, and filtered. The residue was recrystallized from MeOCMe$_3$: the solubility of the meso-form is lower (red crystals). The filtrate was concentrated, the resulting precipitate was filtered off and recrystallized from MeOCMe$_3$ giving 0.2 g (5%) of rac-form (yellow crystalline powder).

rac-form: $^1$H NMR (CDCl$_3$, 20° C.) 7.61 (d, 4H); 7.46 (d, 4H); 7.28 (s, 2H) {C$_{Ar}$—H}; 6.70 (s, 2H, H of C$_5$ ring); 3.46 (s, 6H, —OCH$_3$); 2.31 (s, 6H); 2.20 (s, 6H) {C—CH$_3$}; 1.36 (s, 18H, —C(CH$_3$)$_3$); 1.31 (s, 6H, Si—CH$_3$).

meso-form: $^1$H NMR (CDCl$_3$, 20° C.) δ: 7.57-7.42 (group of m, 10H, C$_{Ar}$—H); 6.58 (s, 2H, H of C$_5$ ring); 3.28 (s, 6H, —OCH$_3$); 2.38 (s, 6H); 2.23 (s, 6H) {C—CH$_3$}; 1.36 (s, 18H, —C(CH$_3$)$_3$); 1.45 (s, 3H); 1.22 (s, 3H) {Si—CH$_3$}.

Catalyst Systems

Preparation of the Catalyst Systems.

All the catalyst solution were prepared following the same recipe: Al$_{TOT}$/Zr=400-800 molar, MAO/TIBA=2 molar, total concentration=50-100 g/L.

Catalyst system S1C-1

C-1/MAO:TIBA 2:1 (Al$_{TOT}$/Zr=600):

39.1 mL of TIBA/isododecane solution (90 g/L) were mixed with 7.4 mL of MAO/toluene solution (Albemarle 30% wt/wt, d=0.928 g/mL, 35.5 mmol MAO) to obtain a MAO/TIBA molar ratio of 2:1. The solution was stirred for 1 h at room temperature and transferred into a 50 mL Schlenk flask containing compound C-1 (55.8 mg, 88.7 µmol). The resulting mixture was diluted with 9.8 mL of isododecane to give a cloudy orange solution. Final concentration: 100 g$_{TOT}$/L and 0.99 g$_{metallocene}$/L.

Catalyst System S2C-2

C-2/MAO:TIBA 2:1 (Al$_{TOT}$/Zr=600):

21.8 mL of TIBA/isododecane solution (110 g/L) were mixed with 5 mL of MAO/toluene solution (Albemarle 30% wt/wt, d=0.928 g/mL, 24 mmol MAO) to obtain a MAO/TIBA molar ratio of 2:1. The solution was stirred for 30 min at room temperature and transferred into a 50 mL Schlenk flask containing C-2 (49.6 mg, 60.4 µmol). The final solution was diluted with 11.7 mL of isododecane to form a dark orange/red solution after overnight stirring at room temperature (final concentration=100 g$_{TOT}$/L and 1.29 g$_{metallocene}$/L).

Catalyst System S3C-2

C-2/MAO:TIBA 2:1 (Al$_{TOT}$/Zr=600):

13 mL of TIBA/isododecane solution (90 g/L) were mixed with 2.5 mL of MAO/toluene solution (Albemarle 30% wt/wt, d=0.928 g/mL, 11.8 mmol MAO) to obtain a MAO/TIBA molar ratio of 2:1. The solution was stirred for 1 h at room temperature and transferred into a 50 mL Schlenk flask containing C-2 (24.2 mg, 29.5 µmol). The final solution was diluted with 22.1 mL of cyclohexane to form a dark orange/red solution after overnight stirring at room temperature (final concentration=50 g$_{TOT}$/L and 0.645 g$_{metallocene}$/L).

Catalyst System S4C-3

C3/MAO:TIBA 2:1 (Al$_{TOT}$/Zr=800):

19.6 mL of TIBA/isododecane solution (110 g/L) were mixed with 4.5 mL of MAO/toluene solution (Albemarle 30% wt/wt, d=0.928 g/mL) to obtain a MAO/TIBA molar ratio of 2:1. The solution was stirred for 1 h at room temperature and transferred into a 50 mL Schlenk flask containing C-3 (33.9 mg, 40.8 µmol). The resulting mixture was diluted with 25.2 mL of isododecane to give a bright orange solution. Final concentration: 70 g$_{TOT}$/L and 0.686 g$_{metallocene}$/L.

Catalyst System S5A-1

A-1/MAO:TIBA 2:1 ($Al_{TOT}/Zr=600$):

32.2 mL of TIBA/isododecane solution (90 g/L) were mixed with 6.1 mL of MAO/toluene solution (Albemarle 30% wt/wt, d=0.928 g/mL, 29 mmol MAO) to obtain a MAO/TIBA molar ratio of 2:1. The solution was stirred for 1 h at room temperature and transferred into a 50 mL Schlenk flask containing A-1 (58.5 mg, 73 µmol). The final solution was diluted with 8.2 mL of isododecane to reach a concentration of 100 $g_{TOT}$/L and 1.26 $g_{metallocene}$/L. The orange mixture contained some gelly precipitate which was removed by decantation.

Catalyst System S6A-1

A-1/MAO:TIBA 2:1 ($Al_{TOT}/Zr=600$):

13.1 mL of TIBA/isododecane solution (90 g/L) were mixed with 2.5 mL of MAO/toluene solution (Albemarle 30% wt/wt, d=0.928 g/mL, 11.9 mmol MAO) to obtain a MAO/TIBA molar ratio of 2:1. The solution was stirred for 1 h at room temperature and transferred into a 50 mL Schlenk flask containing A-1 (23.9 mg, 29.8 µmol). The final solution was diluted with 22.3 mL of isododecane to reach a concentration of 50 $g_{TOT}$/L and 0.629 $g_{metallocene}$/L.

Catalyst System S7A-1

A-1/MAO:TIBA 2:1 ($Al_{TOT}/Zr=800$):

14.5 mL of TIBA/isododecane solution (110 g/L) were mixed with 3.4 mL of MAO/toluene solution (Albemarle 30% wt/wt, d=0.928 g/mL, 16.1 mmol MAO) to obtain a MAO/TIBA molar ratio of 2:1. The solution was stirred for 1 h at room temperature and transferred into a 50 mL Schlenk flask containing A-1 (24.2 mg, 30 µmol). The resulting mixture was diluted with 18.6 mL of isododecane to give a bright orange solution. Final concentration: 70 $g_{TOT}$/L and 0.663 $g_{metallocene}$/L.

Catalyst System S8A-1

A-1/MAO:TIBA 2:1 ($Al_{TOT}/Zr=400$):

13.7 mL of TIBA/cyclohexane solution (113 g/L) were mixed with 3.3 mL of MAO/toluene solution (Albemarle 30% wt/wt, d=0.92 g/mL, 15.6 mmol MAO) to obtain a MAO/TIBA molar ratio of 2:1. The solution was stirred for 1 h at room temperature and transferred into a 50 mL Schlenk flask containing A-1 (46.85 mg, 58.5 µmol). The final solution was diluted with 18.7 mL of cyclohexane. Final mixture concentration=70 $g_{TOT}$/L and 1.313 $g_{metallocene}$/L; color=orange solution.

Catalyst System S9C-4

C-4/MAO:TIBA 2:1 ($Al_{TOT}/Zr=600$):

13.5 mL of TIBA/cyclohexane solution (113 g/L) were mixed with 3.2 mL of MAO/toluene solution (Albemarle 30% wt/wt, d=0.92 g/mL, 15.3 mmol MAO) to obtain a MAO/TIBA molar ratio of 2:1. The solution was stirred for 1 h at room temperature and transferred into a 50 mL Schlenk flask containing C-4 (28.4 mg, 38.3 µmol). The final solution was diluted with 7.7 mL of cyclohexane. Final mixture concentration=100 $g_{TOT}$/L and 1.165 $g_{metallocene}$/L; color=dark red solution.

Polymerization Tests

The polymerization procedure and conditions for each test are described below in detail, the polymerization data are reported in Table 1 (polypropylene examples) and table 3 (ethylene-propylene copolymer examples).

The results from the analysis performed on the polymer samples are reported in Table 2 (polypropylene examples) and Table 3 (ethylene-propylene copolymer examples).

Comparative Example 1

A 4.4 L jacketed stainless-steel autoclave, equipped with a mechanically driven stirrer and a 35-mL stainless-steel vial and connected to a thermostat for temperature control, was previously purified by washing with an Al(i-Bu)$_3$ solution in hexane and dried at 50° C. in a stream of nitrogen.

6 mmol of Al(i-Bu)$_3$ (as a 100 g/L solution in hexane), 629 g of cyclohexane, and 732 g of propylene were charged at room temperature, in order to obtain in the polymerization conditions, a liquid composition 50/50 propylene/cyclohexane (wt/wt). The autoclave was then thermostated at the polymerization temperature, 100° C., corresponding for this composition at a pressure of 30.5 bar-g.

5 mL of the catalyst system S1C-1 containing the catalyst/cocatalyst mixture (0.99 mg metallocene/mL solution) was injected in the autoclave by means of 4 mL of cyclohexane through the stainless-steel vial. Propylene was continuously fed for 30 minutes to maintain the pressure at 30.5 bar-g for a total consumption of 44 grams of propylene.

The pressure into the autoclave was decreased until 20 bar, the bottom discharge valve was opened and the polymer was discharged into a heated steel tank containing water at 70° C. The tank heating was switched off and a flow of nitrogen at 0.5 bar-g was fed. After cooling at room temperature, the steel tank was opened and the wet polymer collected. The wet polymer was dried in an oven under reduced pressure at 70° C. Polymerization data are reported on table 1, polymer analysis is reported on table 2.

Comparative Example 2

The procedure of comparative example 1 was repeated feeding 693 g of cyclohexane and 677 g of propylene in order to obtain, at 120° C. and 36 bar-g, a liquid composition of 50/50% wt propylene/cyclohexane.

5 mL of the catalyst system SIC-1 containing the catalyst/cocatalyst mixture (0.99 mg metallocene/mL solution) was injected in the autoclave by means of 4 mL of cyclohexane through the stainless-steel vial.

Propylene was continuously fed for 30 minutes to maintain the pressure of 36 bar-g: 19.6 g of propylene were consumed. Polymerization data are reported on table 1, polymer analysis is reported on table 2.

Comparative Example 3

The procedure of comparative example 1 was repeated feeding 732 g of cyclohexane and 820 g of propylene in order to obtain a liquid composition at 100° C., 32 bar-g, corresponding to a liquid composition of 50/50% wt propylene/cyclohexane.

1 mL of the catalyst system S2C-2 containing the catalyst/cocatalyst mixture (1.29 mg metallocene/mL solution) was injected in the autoclave by means of 4 mL of cyclohexane through the stainless-steel vial.

Propylene was continuously fed for 30 minutes to maintain the real pressure of 32 bar-g: 174 g of propylene were consumed.

The polymer was discharged according to the procedure described in the comparative example 1. Polymerization data are reported on table 1, polymer analysis is reported on table 2.

Comparative Example 4

The procedure of comparative example 1 was repeated feeding 693 g of cyclohexane and 677 g of propylene in order to obtain a liquid composition at 120° C., 36 bar-g, corresponding to a liquid composition of 35/75% wt propylene/cyclohexane.

1.5 mL of the catalyst system S3C-2 containing the catalyst/cocatalyst mixture (0.645 mg metallocene/mL solution) was injected in the autoclave by means of 4 mL of cyclohexane through the stainless-steel vial.

Scarce reactivity was observed in this reaction, thus there was no need to feed additional propylene in the reactor to maintain the real pressure of 36 bar-g. After 30 minutes the polymer was discharged according to the procedure described in the comparative example. Polymerization data are reported on table 1, polymer analysis is reported on table 2.

Example 5

The procedure of comparative example 1 was repeated feeding 732 g of cyclohexane and 820 g of propylene in order to obtain a liquid composition at 100° C., 32 bar-g, corresponding to a liquid composition of 50/50% wt propylene/cyclohexane.

4 mL of the catalyst system S5A-1 containing the catalyst/cocatalyst mixture (0.629 mg metallocene/mL solution) was injected in the autoclave by means of 4 mL of cyclohexane through the stainless-steel vial.

Propylene was continuously fed for 30 minutes to maintain the real pressure of 32 bar-g: 14 g of propylene were consumed.

The polymer was discharged according to the procedure described in the comparative example 1. Polymerization data are reported on table 1, polymer analysis is reported on table 2.

Example 6

The procedure of comparative example 1 was repeated feeding 693 g of cyclohexane and 677 g of propylene in order to obtain a liquid composition at 120° C., 36 bar-g, corresponding to a liquid composition of 35/75% wt propylene/cyclohexane.

2.5 mL of the catalyst system S6A-1 containing the catalyst/cocatalyst mixture (1.26 mg metallocene/mL solution) was injected in the autoclave by means of 4 mL of cyclohexane through the stainless-steel vial.

Propylene was continuously fed for 30 minutes to maintain the real pressure of 36 bar-g: 16 g of propylene were consumed.

The polymer was discharged according to the procedure described in the comparative example 1. Polymerization data are reported on table 1, polymer analysis is reported on table 2.

TABLE 1

| Ex | Cat. Sys. | $T_{POL}$ (° C.) | P (bar-g) | t (min) | initial mass of Propylene (g) | $kg_{POL}/(g * 30')$ |
|---|---|---|---|---|---|---|
| 1* | S1C-1 | 100 | 31.5 | 40 | 732 | 6.8 |
| 2* | S1C-1 | 120 | 37 | 30 | 677 | 5.1 |
| 3* | S2C-2 | 100 | 32 | 30 | 820 | 136 |
| 4* | S3C-2 | 120 | 36 | 30 | 677 | 20.7 |
| 5 | S5A-1 | 100 | 32 | 30 | 732 | 121 |
| 6 | S6A-1 | 120 | 36 | 30 | 677 | 15.3 |

Activity in kg of polymer per gram of metallocene averaged over 30 minutes.
*= comparative.

TABLE 2

| Ex | MC | $T_m$ (° C.) | mmmm (%) | mrrm (%) | 2.1 (%) | 3.1 (%) | $M_w$ kg/mol | $M_w/M_n$ |
|---|---|---|---|---|---|---|---|---|
| 1* | C-1 | 154.6 | 96.6 | 0.30 | 0.3 | 0.1 | 246 | 2.3 |
| 2* | C-1 | 148.4 | 95.2 | 0.36 | 0.3 | 0.3 | 92 | 2.5 |
| 3* | C-2 | 151.7 | 96.9 | 0.13 | 0.3 | 0.2 | 235 | 2.3 |
| 4* | C-2 | 149.3 | 95.0 | 0.35 | 0.2 | 0.5 | n.a. | n.a. |
| 5 | A-1 | 150.6 | 96.2 | 0 | 0.6 | 0.1 | 717 | 2.7 |
| 6 | A-1 | 147.8 | 93.8 | 0 | 0.6 | 0.5 | 298 | 2.5 |

*= comparative
n.a. = not available

As can be seen from table 2, the molecular weight of the polymers obtained by using the metallocene compound according to the invention are considerably higher than the molecular weight of the polymers obtained with metallocene compounds known in the art. Even if the polymerization runs are carried out at very high temperatures (100° and 120° C.).

Ethylene-Propylene Copolymerizations

Comparative Example 7

The procedure of comparative example 1 was repeated feeding 716 g of cyclohexane, 61 g of ethylene and 631 g of propylene in order to obtain a liquid composition at 100° C., 36 bar-g, corresponding to a liquid composition of 8/92% wt ethylene/propylene.

2 mL of the catalyst system S4C-3 containing the catalyst/cocatalyst mixture (0.686 mg metallocene/mL solution) was injected in the autoclave by means of 4 mL of cyclohexane through the stainless-steel vial.

A constant ethylene/propylene mixture 17/83% wt was continuously fed for 30 minutes to maintain the pressure of 36 bar-g: 20 g of ethylene and 95 g of propylene were consumed.

The polymer was discharged according to the procedure described in the comparative example 1. Polymerization data and polymer analysis are reported on table 3.

Example 8

The procedure of comparative example 1 was repeated feeding 716 g of cyclohexane, 61 g of ethylene and 631 g of propylene in order to obtain a liquid composition at 100° C., 36 bar-g, corresponding to a liquid composition of 8/92% wt ethylene/propylene.

2 mL of the catalyst system S7A-1 containing the catalyst/cocatalyst mixture (0.663 mg metallocene/mL solution) was injected in the autoclave by means of 4 mL of cyclohexane through the stainless-steel vial.

A constant ethylene/propylene mixture 17/83% wt was continuously fed for 30 minutes to maintain the pressure of 36 bar-g: 26 g of ethylene and 126 g of propylene were consumed.

The polymer was discharged according to the procedure described in the comparative example 1. Polymerization data and polymer analysis are reported on table 3.

Comparative Example 9

The procedure of comparative example 1 was repeated feeding 1000 g of cyclohexane, 142.5 g of ethylene, and 137 g of propylene in order to obtain, at 100° C. and 33 bar-g, a liquid composition of 15/85% wt monomers/cyclohexane.

3 mL of the catalyst system S9C-4 containing the catalyst/cocatalyst mixture (1.165 mg metallocene/mL solution) were diluted with 5 mL of cyclohexane, charged in the stainless-steel vial and injected into the autoclave by nitrogen overpressure.

A constant ethylene/propylene mixture 70/30% wt was continuously fed for 30 minutes to maintain the pressure of 33 bar-g: 48 g of ethylene and 20.9 g of propylene were consumed.

Polymerization data and polymer analysis are reported on table 3.

Example 10

The procedure of comparative example 1 was repeated feeding 945 g of cyclohexane, 118 g of ethylene, and 172 g of propylene in order to obtain, at 100° C. and 31 bar-g, a liquid composition of 18/82% wt monomers/cyclohexane. 300 normal mL of hydrogen were charged in the autoclave. 0.8 mL of the catalyst system S8A-1 containing the catalyst/cocatalyst mixture (1.313 mg metallocene/mL solution) were diluted with 5 mL of cyclohexane, charged in the stainless-steel vial and injected into the autoclave by nitrogen overpressure.

A constant ethylene/propylene mixture 70/30% wt was continuously fed for 30 minutes to maintain the pressure of 31 bar-g: 65.5 g of ethylene and 28 g of propylene were consumed. Polymerization data and polymer analysis are reported on table 3.

$Al_{TOT}/Zr=400$, MAO/TIBA=2/1) was then added at room temperature to MAO, obtaining a colourless solution, which was stirred at r.t. for 1 h. Finally this solution in iso-dodecane/toluene was slowly added at room temperature under nitrogen atmosphere to the metallocene, yielding a clear orange-red catalytic solution (after 15 min stirring), which was tested as such in polymerization. The concentration of A-1 resulted to be 2.3 mg of metallocene per mL of solution.

Catalyst S11C-4

47.9 mg of C-1 (64.6 μmol) were charged at room temperature under nitrogen atmosphere into a 50 mL Schlenk flask, equipped with a magnetic stirrer. 3.6 mL of MAO Albemarle 30% wt. in toluene (17.24 mmol, $Al_{MAO}/Zr=267$) were charged at room temperature under nitrogen atmosphere into a second 50 mL Schlenk flask. Triisobutylaluminium (TIBA) in iso-dodecane (19 mL, conc. 90 g/L, 8.58 mmol, $Al_{TIBA}/Zr=133$, $Al_{TOT}/Zr=400$, MAO/TIBA=2/1) was then added at room temperature to MAO, obtaining a colourless solution, which was stirred at r.t. for 1 h. Finally this solution in iso-dodecane/toluene was slowly added at room temperature under nitrogen atmosphere to the metallocene, yielding a clear orange-red catalytic solution (after 15 min stirring), which was tested as such in polymerization. The concentration of C-1 resulted to be 2.12 mg of metallocene per mL of solution.

Propylene/1-hexene Copolymerizations 100 mL of isododecane and 0.8 mmol of TIBA were charged at room temperature in a 250 ml Buchi glass reactor, equipped with magnetically driven stirrer and a stainless-steel connectors valves, in a thermostat for temperature control, previously purified by washing with a 10% wt/vol TIBA solution in hexanes.

TABLE 3

| Ex | Cat. Sys. | $T_{POL}$ (° C.) | P (bar-g) | initial mass of Ethylene (g) | initial mass of Propylene (g) | ethylene/propylene wt/wt feed ratio | Activity $kg_{POL}/(g * 30')$ | ethylene (% wt) | I.V. (dL/g) |
|---|---|---|---|---|---|---|---|---|---|
| 7* | S4C-3 | 100 | 36 | 61 | 631 | 17/83 | 215 | 11.3 | 0.76 |
| 8 | S7A-1 | 100 | 36 | 61 | 631 | 17/83 | 137 | 11.3 | 2.78 |
| 9* | S9C-4 | 100 | 33 | 142.5 | 137 | 70/30 | 20.6 | 67.2 | 1.88 |
| 10 | S8A-1 | 100 | 31 | 118 | 172 | 70/30 | 147.5 | 66.4 | 2.46 |

Activity in kg of polymer per gram of metallocene averaged over 30 minutes.
*Comparative
n.a. = not available By comparing example 7 and example 8, and example 9 and example 10, it is clear that the molecular weight of the copolymers obtained in examples 8 and 10 are higher than the molecular weight of the copolymers obtained in examples 7 and 9.

Copolymerizations with Propylene and Higher Alpha Olefins

Catalyst S10A-1

21 mg of A-1 (26.3 μmol) were charged at room temperature under nitrogen atmosphere into a 50 mL Schlenk flask, equipped with a magnetic stirrer. 1.47 mL of MAO Albemarle 30% wt. in toluene (7.0 mmol, $Al_{MAO}/Zr=267$) were charged at room temperature under nitrogen atmosphere into a second 50 mL Schlenk flask. Triisobutylaluminium (TIBA) in iso-dodecane (7.7 mL, conc. 90 g/L, 3.5 mmol, $Al_{TIBA}/Zr=133$, The amount of 1-hexene reported in table 1 was injected in the autoclave that was then thermostated at the polymerization temperature (90° C.). The solution containing the catalyst/cocatalyst mixture containing the amount of metallocene compound reported in table 1 was injected in the autoclave by syringe at 1 bar of pressure of monomer then the pressure was increased at 7 bar-g of propylene, and the polymerization carried out at constant temperature for the time indicated in table 1. Then stirring was interrupted, the pressure was released to ambient pressure, and the autoclave was opened. At r.t. the solution mixture was discharged into a beaker containing acetone. The polymer was isolated by filtration and then dried in an oven under reduced pressure at 70° C. The polymerization conditions are reported in table 4 and the polymerization results are reported in table 5.

TABLE 4

| Ex. | Catalyst | mg | 1-Hexene (g) | t (min) |
|---|---|---|---|---|
| cop1* | S11C-4 | 0.79 | 6.78 | 45 |
| cop2* | S11C-4 | 0.68 | 3.39 | 20 |
| cop3* | S11C-4 | 0.52 | 1.7 | 18 |
| cop4* | S11C-4 | 0.34 | — | 25 |
| cop5 | S10A-1 | 1.15 | 6.78 | 12 |
| cop6 | S10A-1 | 0.81 | 3.39 | 4 |
| cop7 | S10A-1 | 0.58 | 1.7 | 7 |
| cop8 | S10A-1 | 0.41 | — | 9 |

*comparative

TABLE 5

| Ex. | Yield (g) | C6 Polymer (NMR) % wt | kg/$g_{MC}$/h | I.V. (dL/g, THN) | $T_m$ °C |
|---|---|---|---|---|---|
| cop1* | 5.3 | 36.6 | 9.0 | 0.85 | n.d. |
| cop2* | 2.18 | 23.4 | 9.6 | 0.99 | 45.5[a] |
| cop3* | 3.2 | 10.2 | 20.4 | 1.10 | 99.3 |
| cop4* | 4.05 | — | 28.8 | 1.46 | 155.4 |
| cop5 | 3.63 | 35.8 | 15.6 | 1.21 | n.d. |
| cop6 | 1.17 | 25.5 | 21.6 | 1.51 | n.d. |
| cop7 | 2.2 | 13.0 | 33.0 | 2.05 | 85.9 |
| cop8 | 3.0 | — | 48.6 | 4.77 | 148.2 |

*comparative
n.d. = no melting peak detectable
[a] = broad melting transition showing crystallization during heating Propylene/1-butene Copolymerizations A 4.4 L jacketed stainless-steel autoclave, equipped with a mechanical stirrer and a 50-mL stainless-steel vial, was purified by washing with an Al(i-Bu)$_3$ solution in hexane and dried at 70° C. in a stream of nitrogen.

23.8 mL of a 100 g/L TIBA/hexane solution (corresponding to 12 mmol of TIBA), 670 g of cyclohexane, 557 g of propylene and 186 g of butene were charged into the autoclave, and heated to 90° C., giving a liquid composition of 50/50 (wt/wt) monomers/cyclohexane, and a pressure of 24 bar-g. 2.6 mL of the catalyst system containing the catalyst/cocatalyst solution S10A-1 was diluted with 5 mL of cyclohexane, charged in the stainless-steel vial and injected into the autoclave by nitrogen overpressure.

A constant propylene/butene mixture 80/20% wt was continuously fed for 60 minutes to maintain the pressure at 24 bar-g for a total consumption of 125 g of propylene and 31.5 g of butene.

The pressure into the autoclave was increased with nitrogen to 30 bar-g, the bottom discharge valve opened and the polymer discharged into a heated steel tank and treated for 10 min with water steam. The tank heating was switched off and a flow of nitrogen at 0.5 bar-g was fed to remove the water. The steel tank was finally opened, the wet polymer collected, and dried overnight under reduced pressure at 70° C.

244 of polymer were obtained, corresponding to a productivity of 72 kg$_{Pol}$/g$_{metallocene}$.

The polymer contains 18.4 wt % butene by $^{13}$C NMR analysis, has an intrinsic viscosity of 2.0 dL/g and its melting point (second melting) is 109° C.

The invention claimed is:
1. A bridged metallocene compound of formula (I):

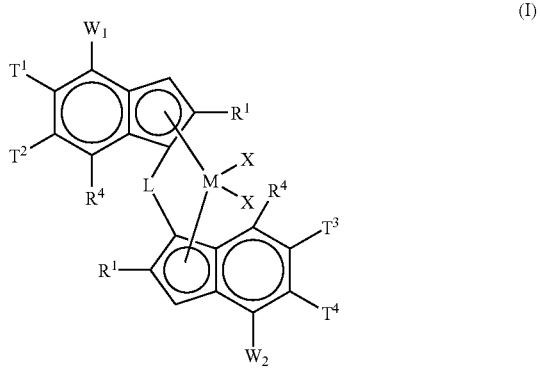

wherein:
M is an atom of a transition metal selected from those belonging to group 3, 4, or to the lanthanide or actinide groups in the Periodic Table of the Elements;

X, equal to or different from each other, is a hydrogen atom, a halogen atom, a R, OR, OSO$_2$CF$_3$, OCOR, SR, NR$_2$ or PR$_2$ group wherein R is a linear or branched, cyclic or acyclic, C$_1$-C$_{40}$-alkyl, C$_2$-C$_{40}$ alkenyl, C$_2$-C$_{40}$ alkynyl, C$_6$-C$_{40}$-aryl, C$_7$-C$_{40}$-alkylaryl or C$_7$-C$_{40}$-arylalkyl radical; optionally containing heteroatoms belonging to groups 13-17 of the Periodic Table of the Elements; or two X groups can be joined together to form a group OR'O wherein R' is a C$_1$-C$_{20}$-alkylidene, C$_6$-C$_{20}$-arylidene, C$_7$-C$_{20}$-alkylarylidene, or C$_7$-C$_{20}$-arylalkylidene radical;

L is a divalent bridging group selected from C$_1$-C$_{20}$ alkylidene, C$_3$-C$_{20}$ cycloalkylidene, C$_6$-C$_{20}$ arylidene, C$_7$-C$_{20}$ alkylarylidene, or a C$_7$-C$_{20}$ arylalkylidene radicals, optionally containing heteroatoms belonging to groups 13-17 of the Periodic Table of the Elements, or it is a silylidene radical containing up to 5 silicon atoms;

R$^1$ is a linear C$_1$-C$_{40}$ hydrocarbon radical optionally containing heteroatoms belonging to groups 13-17 of the Periodic Table of the Elements;

T$^1$ and T$^4$, equal to or different from each other, are an OR$^2$, wherein R$^2$, equal to or different from each other, is a C$_1$-C$_{40}$ hydrocarbon radical;

T$^2$ and T$^3$, equal to or different from each other, are linear or branched, C$_1$-C$_{70}$-alkyl radicals;

R$^4$ is a hydrogen atom or C$_1$-C$_{40}$ hydrocarbon radical optionally containing heteroatoms belonging to groups 13-17 of the Periodic Table of the Elements; and W$^1$ and W$^2$, equal or different from each other, are an aromatic 5 or 6 membered ring optionally containing heteroatoms belonging to groups 15-16 of the Periodic Table of the Elements; the valence of each atom of said ring is substituted with hydrogen atom or it can optionally be substituted with R$^5$ groups, wherein R$^5$, equal to or different from each other, are C$_1$-C$_{40}$ hydrocarbon radicals optionally containing heteroatoms belonging to groups 13-17 of the Periodic Table of the Elements.

2. The bridged metallocene compound according to claim 1 wherein M is zirconium, titanium or hafnium; X is a hydrogen atom, a halogen atom, an OR'O or R group; and L is Si(R$^{11}$)$_2$ wherein R$^{11}$ is a linear or branched, cyclic or acyclic, C$_1$-C$_{40}$-alkyl, C$_2$-C$_{40}$ alkenyl, C$_2$-C$_{40}$ alkynyl, C$_6$-C$_{40}$-aryl, C$_7$-C$_{40}$-alkylaryl or C$_7$-C$_{40}$-arylalkyl radical.

3. The bridged metallocene compound according to claim 1 wherein $W^1$ and $W^2$ are selected from the group comprising the following moieties of formula (Wa), (Wb) and (Wc):

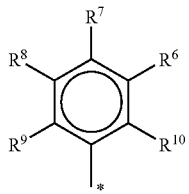
(Wa)

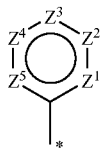
(Wb)

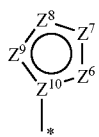
(Wc)

wherein the * represents the point in which the moiety bounds the indenyl moiety of the compound of formula (I);

$R^6$, $R^7$, $R^8$, $R^9$ and $R^{10}$, equal to or different from each other, are hydrogen atoms or $C_1$-$C_{40}$ hydrocarbon radicals optionally containing heteroatoms belonging to groups 13-17 of the Periodic Table of the Elements;

$Z^1$ is a nitrogen atom or a $CR^{10}$ group; $Z^2$ is a nitrogen atom or a $CR^6$ group; $Z^3$ is a nitrogen atom or a $CR^7$ group; $Z^4$ is a nitrogen atom or a $CR^8$ group; $Z^5$ is a nitrogen atom or a $CR^9$ group; provided that no more than 2 groups among $Z^1$, $Z^2$, $Z^3$, $Z^4$ and $Z^5$ are nitrogen atoms;

$Z^6$ is an oxygen atom, a sulfur atom, a $NR^{13}$ group or a $CR^{13}$ group; $Z^7$ is an oxygen atom, a sulfur atom, a $NR^{14}$ group or a $CR^{14}$ group; $Z^8$ is an oxygen atom, a sulfur atom, a $NR^{15}$ group or a $CR^{15}$ group; $Z^9$ is an oxygen atom, a sulfur atom, a $NR^{16}$ group or a $CR^{16}$ group;

$Z^{10}$ is a nitrogen atom or a carbon atom that bonds the indenyl moiety of the structure of formula (I); with the proviso that not more than 1 group among $Z^6$, $Z^7$, $Z^8$, $Z^9$ or $Z^{10}$ is a sulfur atom, an oxygen atom or a nitrogen-containing group atom selected from $NR^{13}$, $NR^{14}$, $NR^{15}$, $NR^{16}$, and a nitrogen atom;

$R^{13}$, $R^{14}$, $R^{15}$ and $R^{16}$, equal to or different from each other, are hydrogen atoms or $C_1$-$C_{40}$ hydrocarbon radicals optionally containing heteroatoms belonging to groups 13-17 of the Periodic Table of the Elements.

4. The bridged metallocene compound according to claim 3 wherein in the moiety of formula (Wa), $R^7$ is a $C_1$-$C_{40}$-alkyl radical, and $R^6$, $R^8$, $R^9$ and $R^{10}$ are hydrogen atoms.

5. The bridged metallocene compound according to claim 3 wherein in the moiety of formula (Wa), $R^{10}$ and $R^8$ are $C_1$-$C_{40}$-alkyl radicals, and $R^7$, $R^8$ and $R^9$ are hydrogen radicals.

6. The bridged metallocene compound according to claim 3 wherein in the moiety of formula (Wa), $R^6$, $R^7$ and $R^8$ are linear or branched $C_1$-$C_{40}$-alkyl radicals and $R^{10}$ and $R^9$ are hydrogen atoms.

7. The bridged metallocene compound according to claim 3 wherein in the moiety of formula (Wa), $R^6$, $R^7$, $R^8$, $R^9$ and $R^{10}$ are hydrogen atoms.

8. The bridged metallocene compound according to claim 3 having formula (IIa):

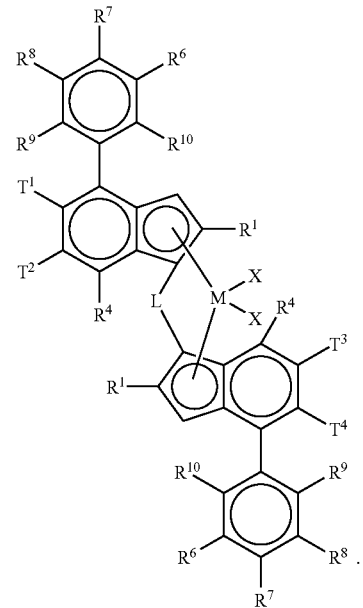
(IIa)

* * * * *